US007749537B2

(12) United States Patent
Hite et al.

(10) Patent No.: US 7,749,537 B2
(45) Date of Patent: Jul. 6, 2010

(54) METHOD OF FORMING A TABLET

(75) Inventors: Michael Hite, Seattle, WA (US); Cathy Federici, Seattle, WA (US); Alan Brunelle, Woodinville, WA (US); Stephen Turner, Snoqualmie, WA (US)

(73) Assignee: SCOLR Pharma, Inc., Bellevue, WA (US)

( * ) Notice: Subject to any disclaimer, the term of this patent is extended or adjusted under 35 U.S.C. 154(b) by 320 days.

(21) Appl. No.: 11/906,303

(22) Filed: Oct. 1, 2007

(65) Prior Publication Data

US 2008/0131507 A1  Jun. 5, 2008

Related U.S. Application Data

(63) Continuation-in-part of application No. 11/633,322, filed on Dec. 4, 2006.

(51) Int. Cl.
*A61K 9/20* (2006.01)
*A61K 31/192* (2006.01)

(52) U.S. Cl. .............. 424/468; 514/568; 514/770; 514/781; 514/570; 424/465; 424/464; 424/480; 424/482; 424/481; 424/462; 424/461; 424/458; 424/457; 424/456

(58) Field of Classification Search .............. None
See application file for complete search history.

(56) References Cited

U.S. PATENT DOCUMENTS

| 4,389,393 A | 6/1983 | Schor et al. |
| 4,609,675 A * | 9/1986 | Franz .......................... 514/568 |
| 4,814,181 A | 3/1989 | Jordan et al. |
| 4,871,548 A | 10/1989 | Edgren et al. |
| 4,877,620 A | 10/1989 | Loew et al. |
| 4,916,161 A | 4/1990 | Patell |
| 4,937,080 A | 6/1990 | Appelgren et al. |
| 4,990,535 A | 2/1991 | Cho et al. |
| 5,087,454 A | 2/1992 | Duerholz et al. |

(Continued)

FOREIGN PATENT DOCUMENTS

CN   1246795   2/1998

(Continued)

OTHER PUBLICATIONS

International Search Report corresponding to International Application No. PCT/US05/35630 dated Apr. 19, 2006.

(Continued)

*Primary Examiner*—Johann R Richter
*Assistant Examiner*—Hong Yu
(74) *Attorney, Agent, or Firm*—RatnerPrestia

(57) ABSTRACT

A method of forming a tablet includes the steps of pre-blending an active pharmaceutical ingredient susceptible to tackiness and a blending additive with a first mixing effort to form a pre-blend mixture, wherein the first mixing effort and a second mixing effort, resulting from mixing at least one excipient with the pre-blend mixture, form a blend suitable for direct compression and compressing the blend to form the tablet. One way of achieving the first mixing effort is to pre-blend for an extended period of time. The method allows for directly compressing the blend without the need for a granulation step or roller compression. One such active pharmaceutical ingredient susceptible to tackiness is ibuprofen.

20 Claims, 24 Drawing Sheets

U.S. PATENT DOCUMENTS

| | | | |
|---|---|---|---|
| 5,100,675 A | 3/1992 | Cho et al. | |
| 5,104,648 A | 4/1992 | Denton et al. | |
| 5,415,871 A | 5/1995 | Pankhania et al. | |
| 5,429,825 A | 7/1995 | Reo et al. | |
| 5,462,747 A | 10/1995 | Radebaugh et al. | |
| 5,512,300 A | 4/1996 | Weng et al. | |
| 5,739,165 A | 4/1998 | Makino et al. | |
| 5,830,503 A * | 11/1998 | Chen | 424/480 |
| 6,358,525 B1 | 3/2002 | Guo et al. | |
| 6,548,083 B1 | 4/2003 | Wong et al. | |
| 6,592,901 B2 | 7/2003 | Durig et al. | |
| 6,599,531 B2 | 7/2003 | Kushla et al. | |
| 6,623,756 B1 | 9/2003 | Wilber et al. | |
| 6,936,632 B2 | 8/2005 | Striegel et al. | |
| 2002/0034540 A1 | 3/2002 | Price | |
| 2003/0045580 A1 | 3/2003 | Einig | |
| 2003/0068368 A1 | 4/2003 | Kushla et al. | |
| 2003/0153623 A1 | 8/2003 | Kishimoto et al. | |
| 2003/0175341 A1 | 9/2003 | Rampal et al. | |
| 2004/0026578 A1 | 2/2004 | King et al. | |
| 2004/0048924 A1 | 3/2004 | Bunick et al. | |
| 2004/0081701 A1 | 4/2004 | Erkoboni et al. | |
| 2004/0096497 A1 | 5/2004 | Ponder et al. | |
| 2004/0102522 A1 | 5/2004 | Gruber et al. | |
| 2004/0121012 A1 | 6/2004 | Baichwal | |
| 2004/0186122 A1 | 9/2004 | Newman et al. | |
| 2004/0204403 A1 | 10/2004 | Pankhania et al. | |
| 2004/0219220 A1 | 11/2004 | Sherry et al. | |
| 2004/0265378 A1 | 12/2004 | Peng et al. | |
| 2007/0077297 A1 | 4/2007 | Hite et al. | |

FOREIGN PATENT DOCUMENTS

| | | |
|---|---|---|
| CN | 1215989 | 5/1999 |
| DE | 100 03 757 | 8/2001 |
| EP | 0297866 | 1/1989 |
| EP | 1444978 | 8/2004 |
| WO | WO 88/08299 | 11/1988 |
| WO | WO 98/34612 | 8/1998 |
| WO | WO 03/063825 | 8/2003 |
| WO | WO 2006/039692 | 4/2006 |

OTHER PUBLICATIONS

International Search Report corresponding to application No. PCT/US2007/024496 dated Jul. 18, 2007.

International Search Report corresponding to application No. PCT/US2007/024489 dated Aug. 12, 2008.

"FMC Problem Solver and Reference manual (2001 FMC Corporation, Philadelphia, PA)", 1998.

USPTO Office Action for U.S. Appl. No. 11/238,802 mailed on Sep. 30, 2009.

* cited by examiner

METHOD OF FORMING A TABLET

CROSS REFERENCE TO RELATED APPLICATIONS

The present invention is a continuation-in-part of U.S. application Ser. No. 11/633,322, filed Dec. 4, 2006 which is incorporated by reference.

While U.S. patent application Ser. No. 11/633,322 claims priority to U.S. application Ser. Nos. 11/238,802, filed Sep. 29, 2005, and U.S. Provisional Applications Nos. 60/614,932, filed Sep. 30, 2004 and 60/689,631, filed Jun. 10, 2005, the present application does not claim priority to these applications. U.S. patent application Ser. Nos. 11/238,802, 60/614,932, and 60/689,631 are incorporated herein by reference.

FIELD OF THE INVENTION

This invention relates to a method of forming a tablet comprising an active pharmaceutical ingredient and a blending additive.

BACKGROUND OF THE INVENTION

Compression of pharmaceutical compositions is traditionally limited to active pharmaceutical ingredients that possess favorable binding and flow characteristics or is achieved through the process of granulating the active pharmaceutical ingredient with blending additive such as binders and flow agents that facilitate compression. Most dosage forms of active pharmaceutical ingredients that are susceptible to tackiness in the tableting process require a granulation step or the use of roller compression. Such a process adds cost and complexity to the manufacture of even relatively simple formulations and may affect in vivo performance and stability.

Exemplary of this problem is the pharmaceutical active ibuprofen. Ibuprofen is 2-(4-isobutylphenyl)propionic acid and is a non-steroidal anti-inflammatory compound (NSAID), which exhibits high levels of anti-inflammatory, analgesic and antipyretic activities necessary for the effective treatment of rheumatoid arthritis and osteo-arthritis and other inflammatory conditions. Ibuprofen is not directly compressible, and attempts to manufacture ibuprofen directly result in tablets portions thereof which stick to the faces of the tableting press, are too friable for storage or transport, or split into two or more segments when expelled from the tableting press.

To circumvent those manufacturing problems, those skilled in the art employ a granulation step prior to tableting, in which the pharmaceutical active is wet granulated with an excipient, such as a blending additive, to form a granular composition comprising the pharmaceutical active and the blending additive. This granular composition can then blended with further excipients and/or is directly compressible for the manufacture of a suitable solid dosage form. Therefore, a need exists for an alternative to granulation to facilitate the preparation of tablets containing active pharmaceutical ingredients that are susceptible to tackiness.

SUMMARY OF THE INVENTION

To achieve these and other objects, and in view of its purposes, an embodiment of the present invention provides a method of forming a tablet comprising the steps of pre-blending an active pharmaceutical ingredient susceptible to tackiness and a blending additive with a first mixing effort to form a pre-blend mixture, wherein the first mixing effort and a second mixing effort, resulting from mixing at least one excipient with the pre-blend mixture, form a blend suitable for direct compression and compressing the blend to form the tablet.

An embodiment of the present invention includes a method of forming a tablet comprising the steps of a) pre-blending an active pharmaceutical ingredient susceptible to tackiness and a blending additive with a first mixing effort to form a pre-blend mixture; b) blending the pre-blend with at least one excipient with a second mixing effort; c) blending the blend from step b with a second blending additive with a third mixing effort, wherein the first mixing effort, the second mixing effort and the third mixing effort form a blend suitable for direction compression; and d) compressing the blend from step c to form the tablet.

Another embodiment of the present invention includes a method of forming a tablet comprising the steps of pre-blending only ibuprofen and silicon dioxide with a first mixing effort to form a pre-blend mixture, wherein the first mixing effort and a second mixing effort, resulting from mixing at least one excipient with the pre-blend mixture, form a blend suitable for direct compression and compressing the blend to form the tablet.

Another embodiment of the present invention includes a method of forming a tablet consisting essentially the steps of pre-blending only ibuprofen and silicon dioxide with a first mixing effort to form a pre-blend mixture; blending the resulting pre-blend mixture with at least one excipient with a second mixing effort; blending the resulting blend with at least one blending additive with a third mixing effort, wherein the first mixing effort, the second mixing effort and the third mixing effort form a blend suitable for direction compression; and compressing the blend from to form the tablet.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawing. Included in the drawing are the following figures.

DETAILED DESCRIPTION OF THE INVENTION

Figure 1:
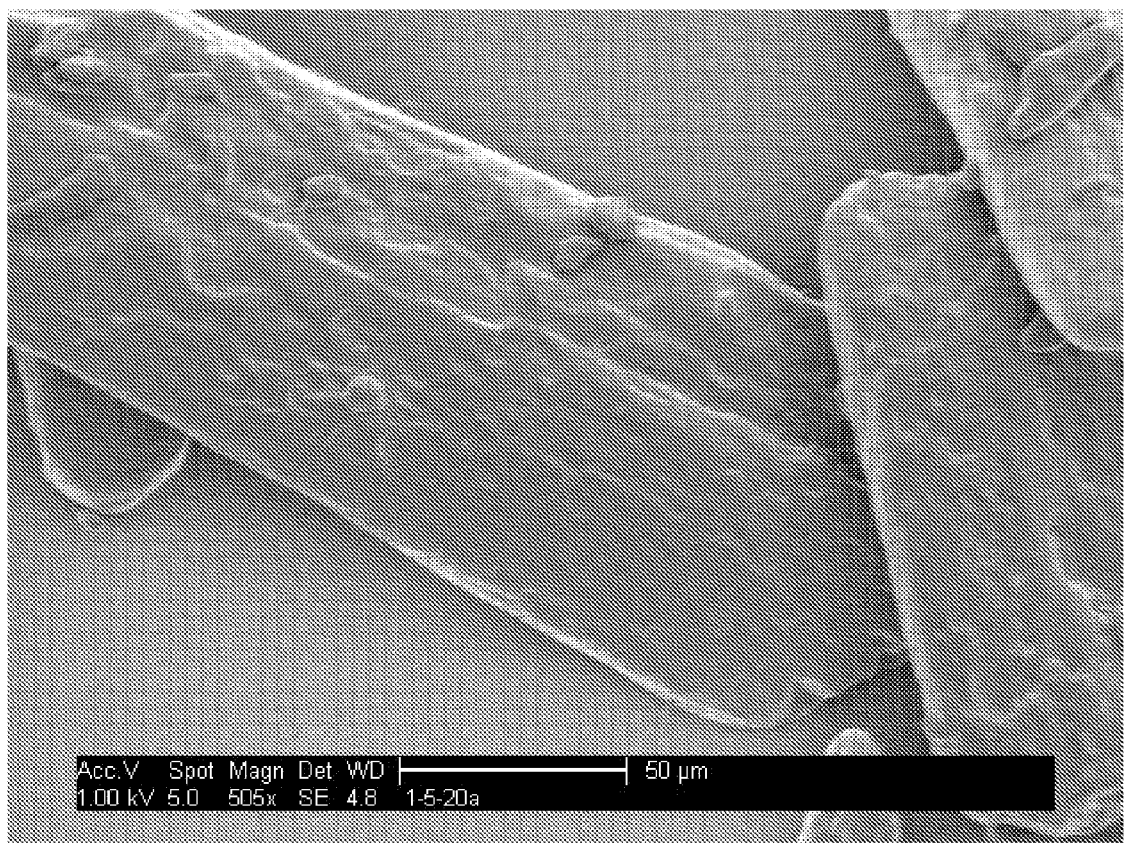
FIG. 1 is a Scanning Electron Micrograph at 500× magnification of unblended Ibuprofen in Example 1.
Figure 2:
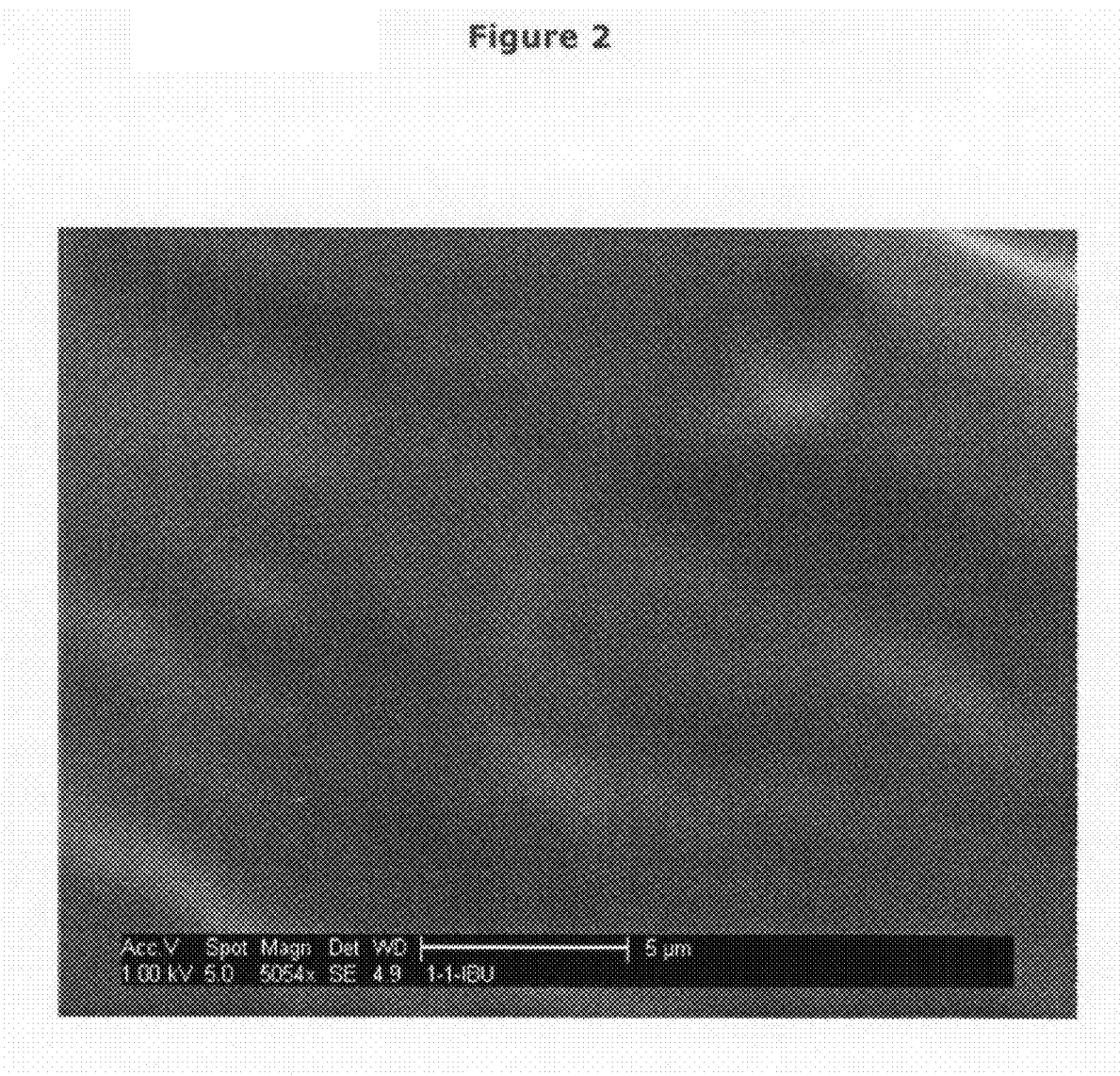
FIG. 2 is a Scanning Electron Micrograph at 5000× magnification of unblended Ibuprofen in Example 1.
Figure 3:
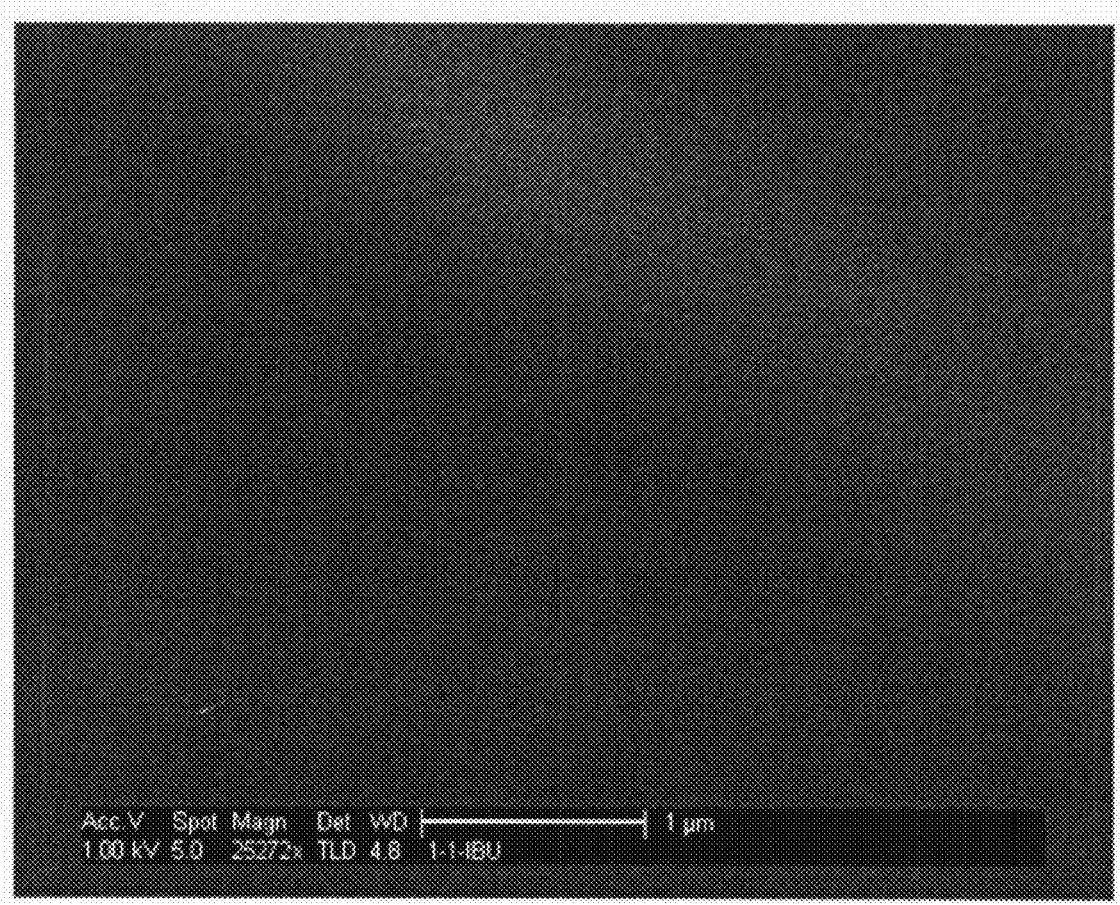
FIG. 3 is a Scanning Electron Micrograph at 25000× magnification of unblended Ibuprofen in Example 1.
Figure 4:
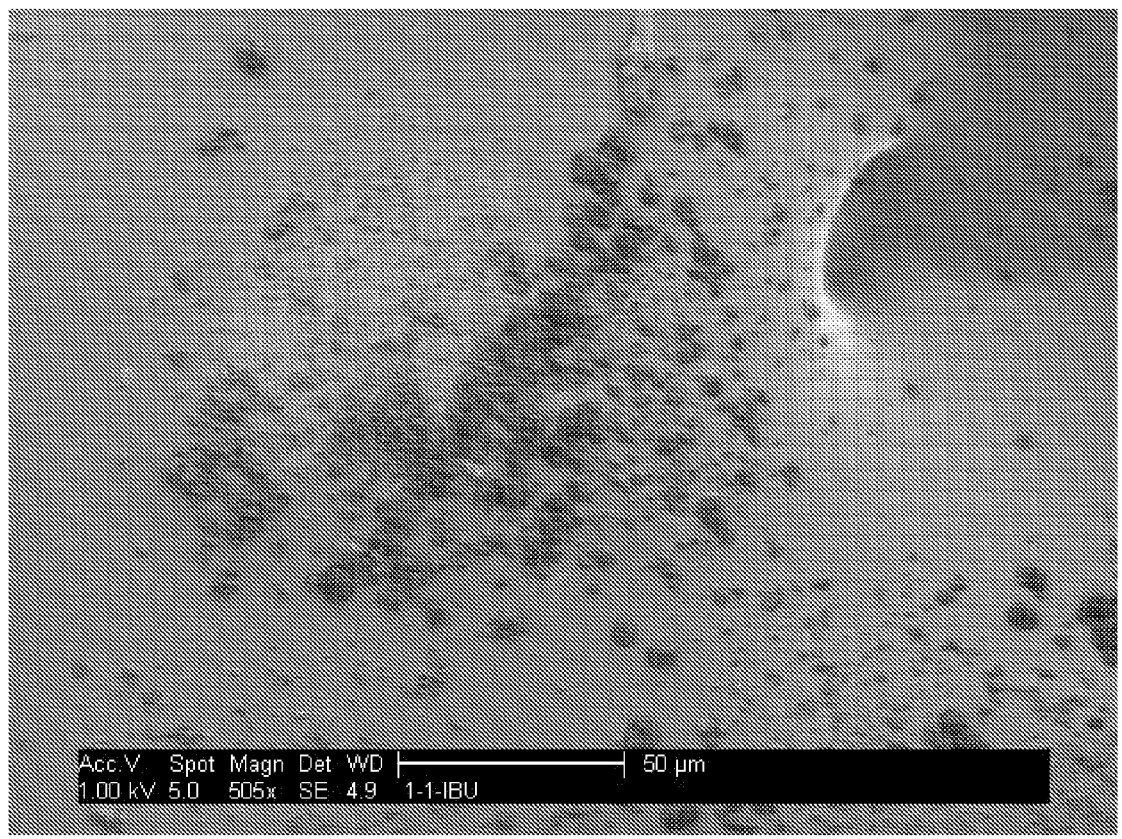
FIG. 4 is a Scanning Electron Micrograph at 500× magnification of unblended silicon-dioxide in Example 1.
Figure 5:
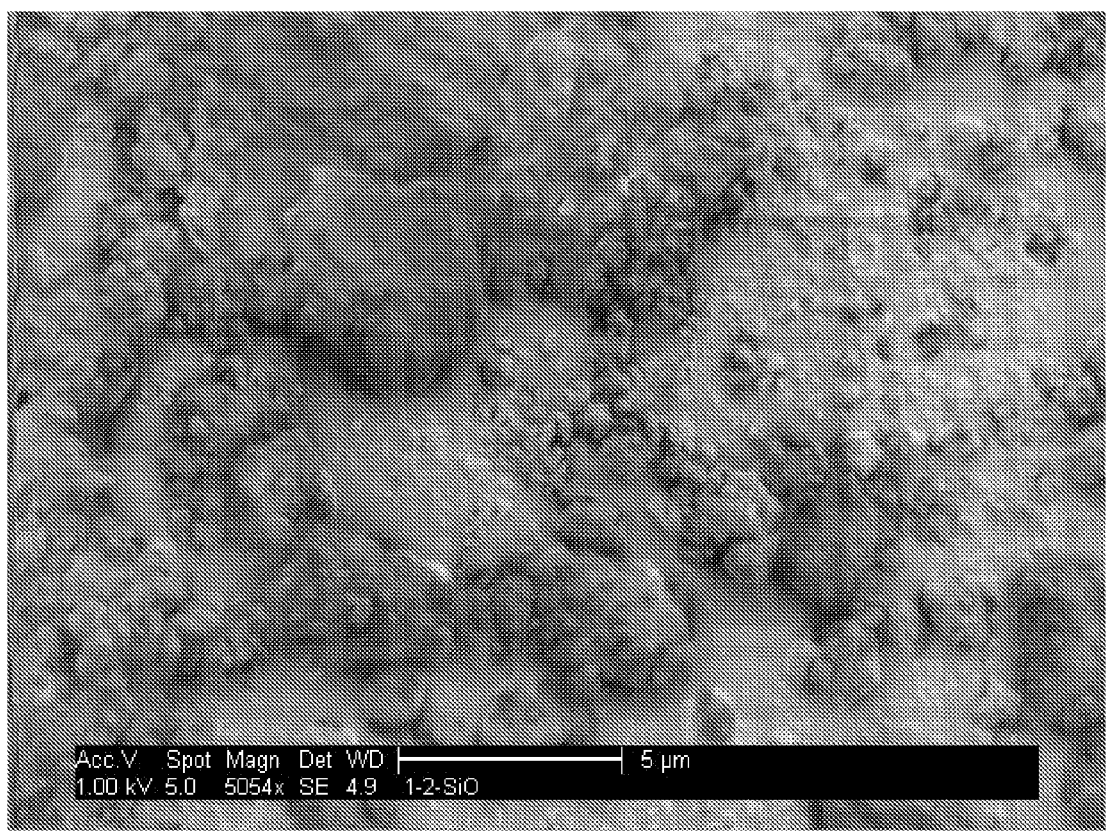
FIG. 5 is a Scanning Electron Micrograph at 5000× magnification of unblended silicon-dioxide in Example 1.
Figure 6:
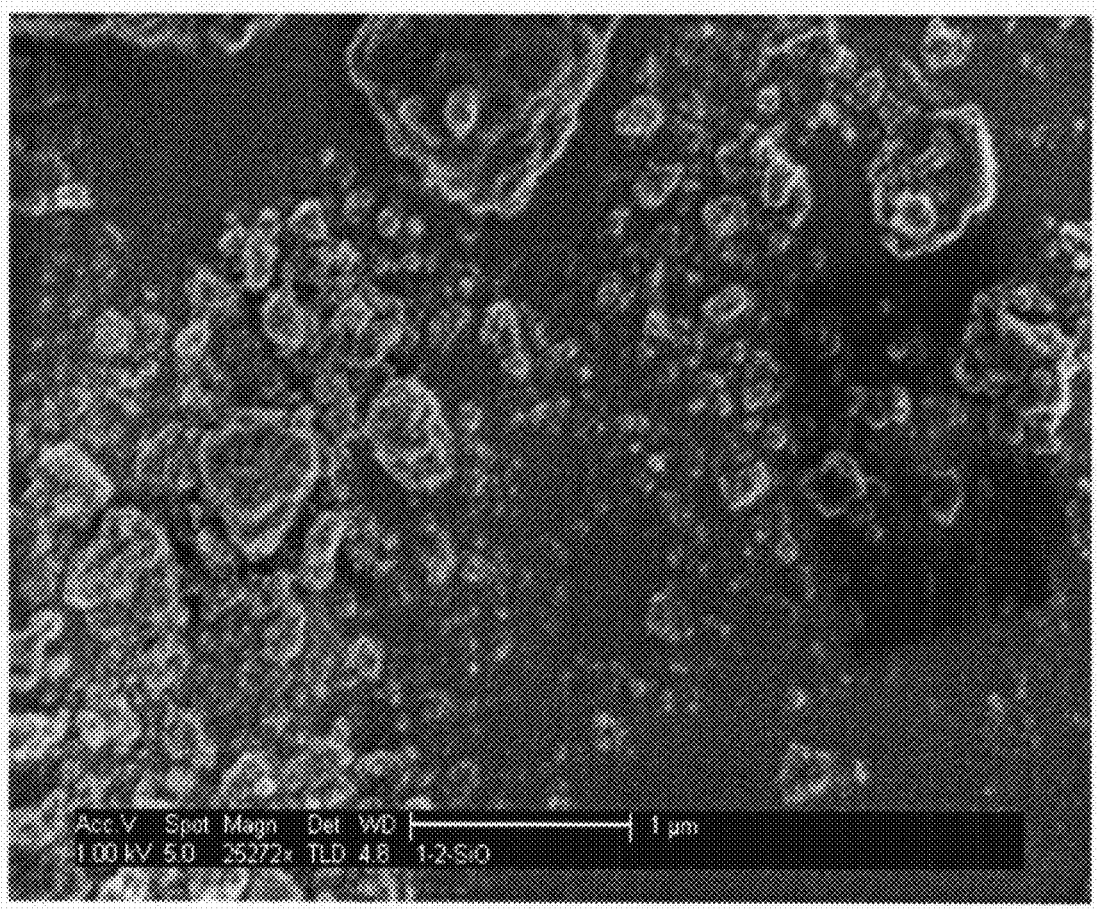
FIG. 6 is a Scanning Electron Micrograph at 25000× magnification of unblended silicon-dioxide in Example 1.

The present invention is further illustrated and described by reference to the following disclosure, examples and discussion below. In the examples and discussion which follow, the use of particular actives, blending additives, excipients, binders, glidants, and flow agents are provided by way of example only and are not intended to limit the scope of this invention.

An embodiment of the present invention includes a method of forming a tablet comprising the steps of a) pre-blending an active pharmaceutical ingredient susceptible to tackiness and a blending additive with a first mixing effort to form a pre-blend mixture; b) blending the pre-blend mixture with at least one excipient with a second mixing effort; c) blending the blend from step b with a second blending additive with a third mixing effort, wherein the first mixing effort, the second mixing effort and the third mixing effort form a blend suitable for direction compression; and d) compressing the blend from step c to form the tablet. According to another embodiment of the present invention, the method can be deemed to consist essentially of these four steps in that the method excludes an additional step, such as granulation or roller compression.

Active pharmaceutical ingredients used in embodiments of this invention include pharmaceutical ingredients susceptible to tackiness. Tackiness is a property which causes, during compression of a blend of the active pharmaceutical in the tableting process, the blend to pick and to foul the tooling. Stated another way, the tackiness causes the blend to stick to the compression faces of the tableting mold. Mathematical models, force-time, force-distance, and die-wall force parameters of tableting are used to describe work of compaction, elasticity, plasticity and time-dependent deformation behavior and various indices of tableting performance such as the bonding index, brittle fracture index, and strain index can be used to predict compaction problems, Patel, S. et al, *Compression Physics in the Formation Development of Tablets* Crit Rev Ther Drug Carrier Syst. 2006; 23(1):1-65, including the tendency of to pick and stick that is seen in materials possessing the quality of tackiness. Many pharmaceutical actives have not yet been characterized by the methods such as the above or may not be known to possess manufacturing problems due to tackiness because traditional formulations have employed wet granulation or another processing step prior to compaction.

Active pharmaceutical ingredients that are often considered susceptible to tackiness include: non-steroidal anti-inflammatory drugs such as acetaminophen, ibuprofen, ketoprofen; antibiotics such as clarithromycin; and nutraceuticals such as glucoseamine and chondriotin.

The invention can potentially be applied to any active pharmaceutical ingredient which demonstrates undesirable picking and sticking due to tackiness of the compound. This can include both known and pharmaceutically useful drugs, nutraceuticals, and other dietary supplements that are compressed into tablets, as well as future counterparts under development for tableted applications.

In one embodiment of this invention, the active pharmaceutical ingredient susceptible to tackiness is ibuprofen. As mentioned above, processes for preparing tablets containing such active pharmaceutical ingredients have typically required a granulation step or the use of roller compression.

According to the present invention, the pre-blending step, when employed with conventional blending steps, referenced as steps b and c above, permit the preparation of tablets containing active pharmaceutical ingredients susceptible to tackiness without a granulation step or roller compression. This is done by imparting an additional mixing effort, described as the "first mixing effort," above to the active pharmaceutical ingredient in the presence of a blending additive. As used herein, a mixing effort is a measure of the work imparted to the ingredients being mixed. Accordingly, mixing effort is a function of a number of factors, including the mixing time, the volume of ingredients used, the particular active pharmaceutical ingredient (including its degree of tackiness), the size of the blender, the type of blender, the speed of blending, and the type and design of paddle used in the blender, among others. To achieve a cumulative mixing effort (i.e. the sum of all of the mixing efforts imparted to the ingredients before compression) sufficient to form a blend suitable for direct compression, it has been found that the time of the pre-blend step, given a particular active pharmaceutical ingredient and blending system, is an independent variable which can be altered to achieve the desired result. In particular, by varying the time of pre-blending, one can easily optimize the formation of tablets without picking. More specifically, it has been found that both too short a time of pre-blending and too great a time of pre-blending lead to unacceptable levels of picking. Given this context, one can empirically determine the optimum time through a trial compression test to determine how significant picking will be given the variables present. A test to determine the potential utility of the invention can include a trial tableting test of the active pharmaceutical ingredient plus excipients in a tableting scale up to the actual commercial scale appropriate for a given product. If the tableting process demonstrates undesirable picking and sticking at any point in the process, this invention can reduce that level of picking and sticking due to tackiness of the active pharmaceutical ingredient and is within the scope of this disclosure. An unacceptable level of picking is one in which a certain percentage of tablets are not suitable for sale due to picking and will vary depending on the particular active ingredient, the cost of the active pharmaceutical ingredients, manufacturing efficiency needs, operator presence, or other arbitrary standards relating to the manufacture of the drug product. For example, typically it would be unacceptable to have more than 10% tablets being deemed unacceptable for sale due to picking. Preferably less than 5%, more preferably less than 1%, and most preferably less than 0.1%, of the tablets made are deemed unsuitable for sale.

Conventionally, blending a pre-blend mixture with at least one excipient is continued until content uniformity is achieved. In addition, blending that resulting blend with a blending additive is conventionally done for a much shorter time (e.g. $\frac{1}{20}^{th}$ of the time). These conventional steps are reflected as steps b and c above. It has been found preferable, in some embodiments, to carry out the pre-blending step for a time slightly increased from the conventional blending of the blending additive and prior to the conventional steps of b and c.

Without being bound by any theory, it appears, as described in connection with the figures below, that the pre-blending step permits the tacky particles of the active pharmaceutical ingredient to be substantially covered by the blending additive. The examples below revealed a progressive pattern of increasing coverage of the ibuprofen crystals by the silicon dioxide (i.e. the blending additive) with the increase of time in the pre-blending step. In a preferable embodiment, pre-blending comprises only ibuprofen and silicon dioxide. In another embodiment, pre-blending comprises ibuprofen, silicon dioxide and silicified microcrystalline cellulose or a combination of silicon dioxide and silicified microcrystalline cellulose (MCC bonded to $SiO_2$). Optionally, additional excipients could be included in the pre-blending step.

Given a particular active pharmaceutical ingredient, blending system and blending times of steps b and c, one can vary the pre-blending time to achieve the desired first mixing effort such that a blend suitable for direct compression following step c is formed. In one embodiment, namely: 1) using ibuprofen as the active pharmaceutical ingredient and silicon dioxide as the blending additive; 2) using a 16 qt V-blender (<1 ft$^3$) at 36 rpm; and 3) having times of 20-60 minutes and 2-15 minutes of mixing times sufficient to achieve content uniformity for steps b and c respectively, a pre-blending time of 20-90 minutes, and preferably 40-60 minutes has been found to optimize the preparation of tablets with minimal picking. In another embodiment, namely: 1) using ibuprofen as the active pharmaceutical ingredient and silicon dioxide as the blending additive; 2) using a 40 ft$^3$ V-blender (<1 ft$^3$) at 10 rpm; and 3) having times of 20-60 minutes and 2-15 minutes of mixing times for steps b and c respectively, a pre-blending time of 20-90 minutes, and preferably 40-60 minutes has been found to optimize the preparation of tablets with minimal picking.

As can be appreciated, a first mixing effort can be identical or different than a second mixing effort. Similarly, in one embodiment, a first mixing effort and a third mixing effort are identical or different. In another embodiment, the second and third mixing effort can be an identical effort or one single mixing effort. In addition, the pre-blending and blending steps can be carried out using conventional equipment.

The tablets formed by this method can be a variety of tablets including but not limited to extended release tablets and immediate release tablets.

Blending additives used in the pre-blending step a or blending step c of this invention include silicon dioxide, silicified microcrystalline cellulose or a combination thereof. In one embodiment silicon dioxide is the blending additive. Microcrystalline cellulose (MCC) of various particles sizes may be used such as: MCC 105 (particle size of about 20 µm), MCC 200 (particle size of about 180 µm) and MCC 302 (particle size of about 90 µm). Other blending additives may be used such as: Prosolv 90 (particle size of about 110 µm) and Prosolv 50 (particle size of about 60 µm); lactose, such as spray dried lactose (Lactopress®); dicalcium phosphate; silica; pregelatinized starch; and combinations thereof. It is desirable to provide a only that amount of blending additive needed to substantially coat the outer surface of the particles of the active pharmaceutical ingredient. In one embodiment the blending additive is present at a concentration in the range of 0.1% to 10% by weight of the active pharmaceutical ingredient. In a preferable embodiment, the blending additive is present at a concentration in the range of 0.5% to 1.5% by weight of the active pharmaceutical ingredient.

Other blending additives may include, but are not limited to, other known glidants such as calcium stearate and magnesium trisilicate; traditional compression aids such as aspartame, dextrose, fructose, maltodextrin, hydrolyzed starches, maltose, mannitol, guar gum, sorbitol, starch sucrose, shellac, talc and xylitol; electrolytes such as sodium chloride and calcium carbonate; hydrophilic polymers such as hydroxy methylcellulose, hydroxypropyl methylcellulose and ethylcellulose; disintegrants such as croscarmellose sodium, crospovidone, gellan gum L-HPC, sodium starch glycolate and carrageenan gums; lubricants such as magnesium stearate, stearic acid, sodium stearyl fumarate and vegetable-based fatty Acids, including mixtures of palmitic and stearic acids; and binders such as carbopol, xanthan gum, povidone and vinyl acetates, including vinyl pyrollidone.

The first and second blending additives may be the same blending additives, different blending additives or a combination of blending additives. In one embodiment the second blending additive is the same blending additive as the first blending additive. In another embodiment, the second blending additive is a combination of silicon dioxide and silicified microcrystalline cellulose and the first blending additive is silicon dioxide. In another embodiment, the second blending additive and the first blending additive is silicon dioxide.

The pre-blend mixture includes the mixture of the active pharmaceutical ingredient and the blending additive resulting from the mixing effort. In one embodiment, the pre-blend mixture includes ibuprofen and silicon dioxide. In another embodiment, the pre-blend mixture includes ibuprofen and silicon dioxide at a concentration of 0.5%-1.5% by weight of the ibuprofen.

Excipients used in blending step b and c above include, but are not limited to flow agents, binders, additives, glidants and tableting aids. Examples of excipients include known glidants; traditional compression aids such as aspartame, dextrose, fructose, maltodextrin, hydrolyzed starches, maltose, mannitol, guar gum, sorbitol, starch sucrose, shellac, talc and xylitol; electrolytes such as sodium chloride and calcium carbonate; hydrophilic polymers such as hydroxy methylcellulose, hydroxypropyl metylcellulose and ethylcellulose; disintegrants such as croscarmellose sodium, crospovidone, gellan gum L-HPC, sodium starch glycolate and carrageenan gums; lubricants such as magnesium stearate, stearic acid, sodium stearyl fumarate and vegetable-based fatty Acids, including mixtures of palmitic and stearic acids; and binders such as carbopol, xanthan gum, povidone and vinyl acetates, including vinyl pyrollidone.

Compression in accordance with this invention, occurs without a granulation step or roller compression whereby a blend resulting from the mixing steps is directly compressed using conventional compression techniques.

Another embodiment of the present invention includes a method of forming a tablet comprising the steps of pre-blending an active pharmaceutical ingredient susceptible to tackiness and a blending additive with a first mixing effort to form a pre-blend mixture, wherein the first mixing effort and a second mixing effort, resulting from mixing at least one excipient with the pre-blend mixture, form a blend suitable for direct compression and compressing the blend to form the tablet.

In this embodiment the second mixing effort is defined differently than the second mixing effort defined in the embodiment described above. In this embodiment the second mixing effort may be inclusive of multiple mixing steps whereby the second mixing effort includes at least one intermediate mixing step between the pre-blending step and the direct compression. The remaining features in this embodiment that are discussed in the embodiment above are consistent with its description above.

In accordance with a process aspect of this invention, manufacture of ibuprofen tablets improved by pre-blending ibuprofen with silicon dioxide or a combination of silicon dioxide and microcrystalline cellulose form. The process of pre-blending ibuprofen with silicon dioxide, or a combination of silicon dioxide and microcrystalline cellulose improves manufacturability of the dosage form and reduces the tendency of the dosage form to fracture, or stick to the faces of the compression machine. The pre-blending duration can range from about 15 minutes to about 60 minutes with significant improvement as blending time is increased to at least 30-40 minutes. Blending can be performed in several different sizes of V-blenders and at several different speeds. In one embodiment, blending can be performed in a 16 qt V-blender (<1 ft$^3$) at 36 rpm while in another embodiment blending can be performed in a 40 ft$^3$ V-blender at 10 rpm. The resulting dry pre-blend, suitably in the form of a finely divided powder, may then blended with the remaining excipients and the resulting composition directly compressed into a satisfactory tableted dosage form.

EXAMPLES

The use of a particular pharmaceutical active and blending additive is not intended to limit the scope of this invention but is exemplary only.

Example 1

Ibuprofen 99% and Silicon Dioxide 1%

Ibuprofen (90-grade, BASF) and silicon dioxide were blended for 60 minutes in a V-type blender. Samples were removed from the V-type blender at 5 minutes, 10 minutes, 20 minutes, 40 minutes, and 60 minutes. All samples removed were retained for analysis.

Analysis was done on a FEI Sirion Scanning Electron Microscope. Controls and experimental samples were applied to double sided tape on SEM support and Au/Pt coated with an SPI Sputter coater, at 5 nm. The data presented in FIGS. 1-21 are examinations at 500×, 5000× and 25000× magnification and illustrate SEM analysis of ibuprofen crystals pre-blended with silicon dioxide at various time intervals.

Figure 22:
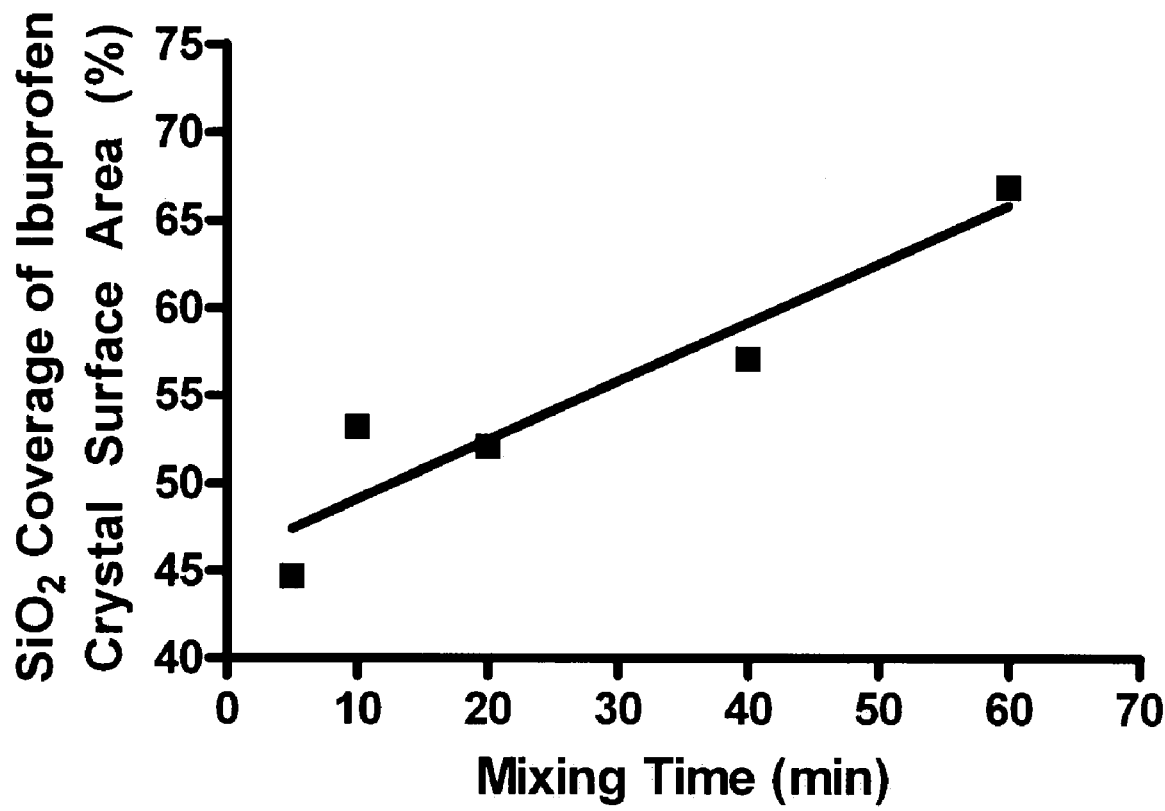
FIG. 22 is a graph illustrating $SiO_2$ Coverage of Ibuprofen.

As shown in FIG. 22, a graph reflecting the SEM analysis, the product of this process revealed a progressive pattern of increasing coverage of the ibuprofen crystals by the silicon dioxide with the increase of time in the pre-blending step. FIG. 22 illustrates a positive correlation between mixing time and surface area coverage of ibuprofen crystals with silicon dioxide as increasing with the increase of mixing time. An increase in surface area coverage of the ibuprofen crystals which are susceptible to tackiness by silicon dioxide decreases the tackiness present in the mixture and thus facilitates direct compression without a granulation step.

Figure 7:
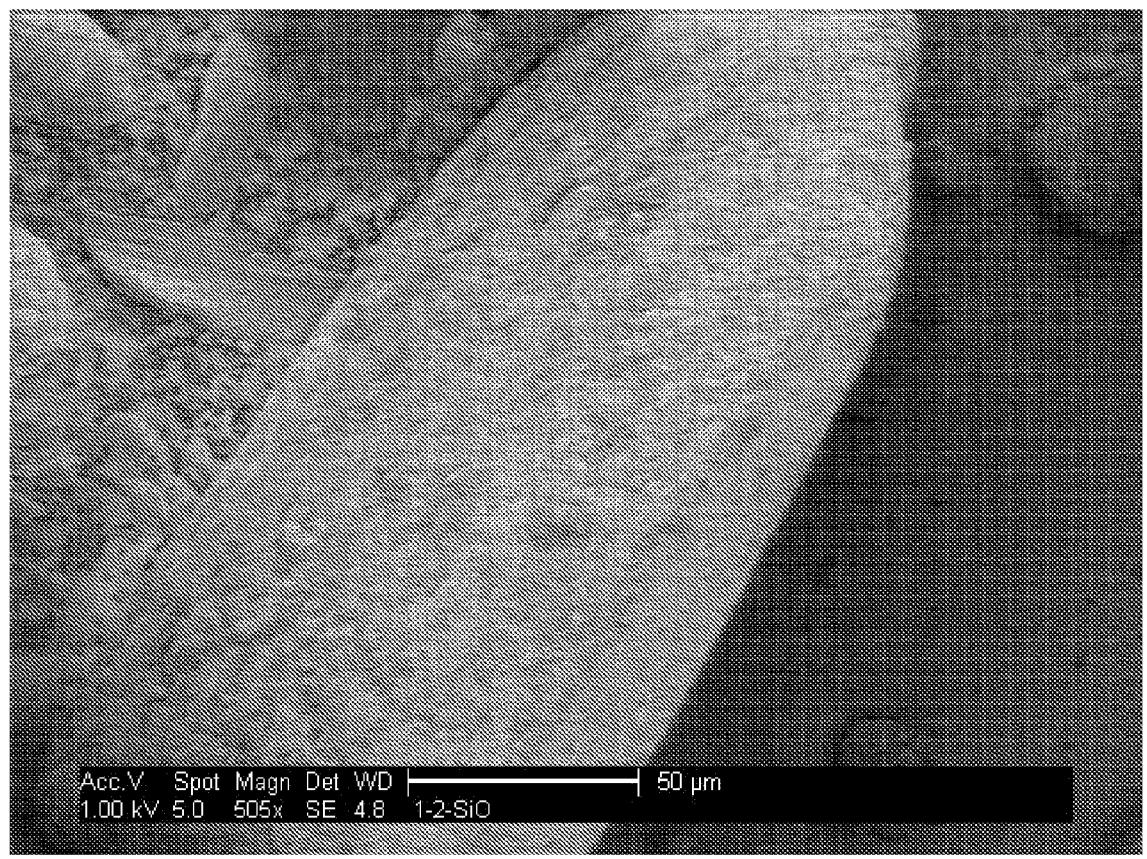
FIG. 7 is a Scanning Electron Micrograph at 500× magnification of ibuprofen/silicon-dioxide blend after 5 minutes in Example 1.
Figure 8:
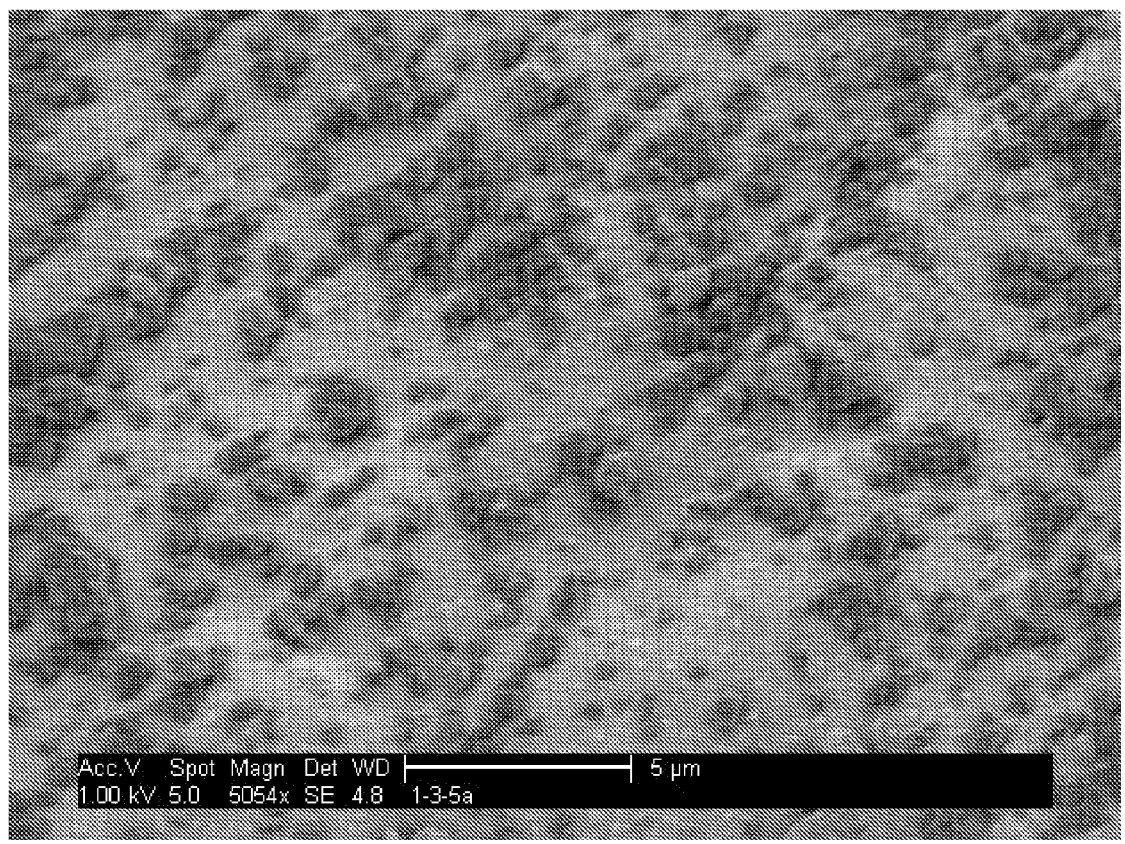
FIG. 8 is a Scanning Electron Micrograph at 5000× magnification of ibuprofen/silicon-dioxide blend after 5 minutes in Example 1.
Figure 9:
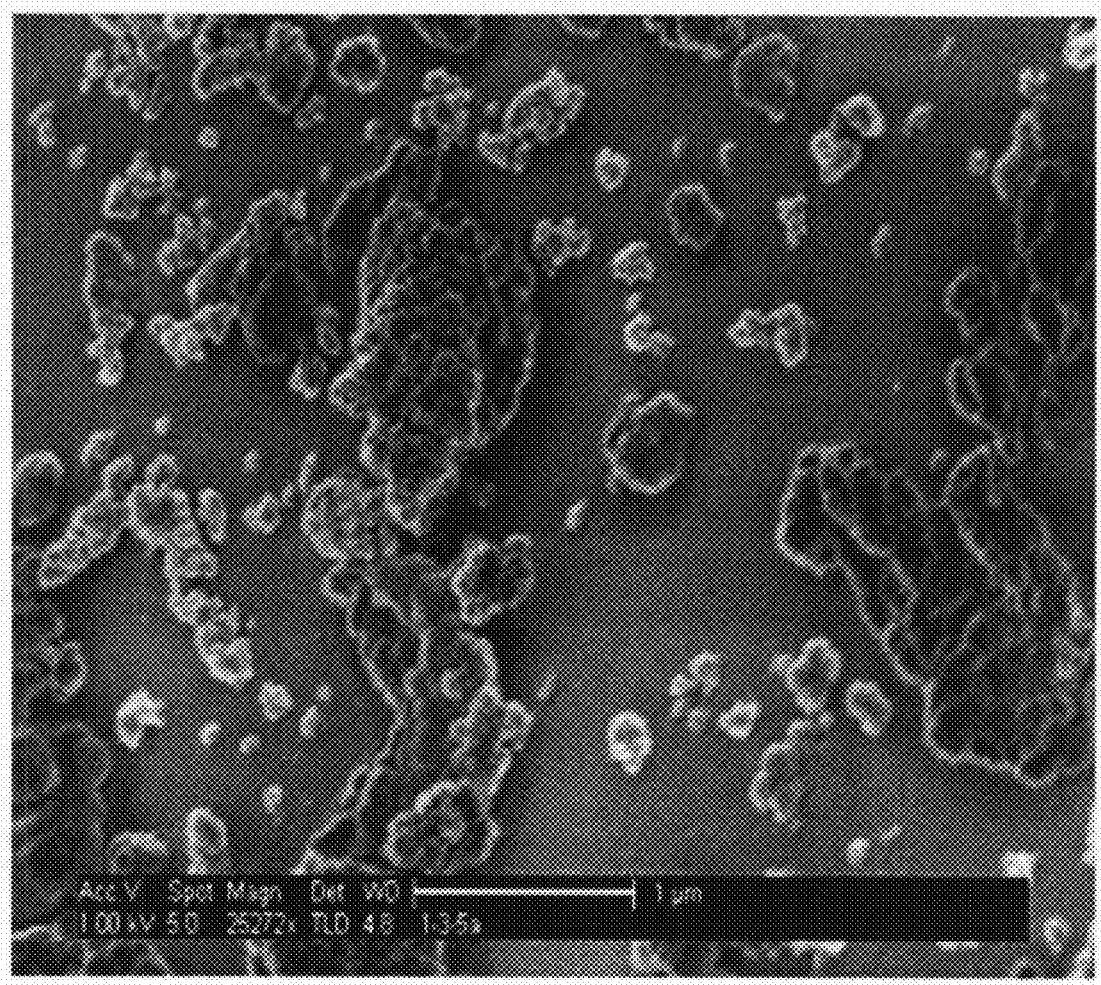
FIG. 9 is a Scanning Electron Micrograph at 25000× magnification of ibuprofen/silicon-dioxide blend after 5 minutes in Example 1.
Figure 10:
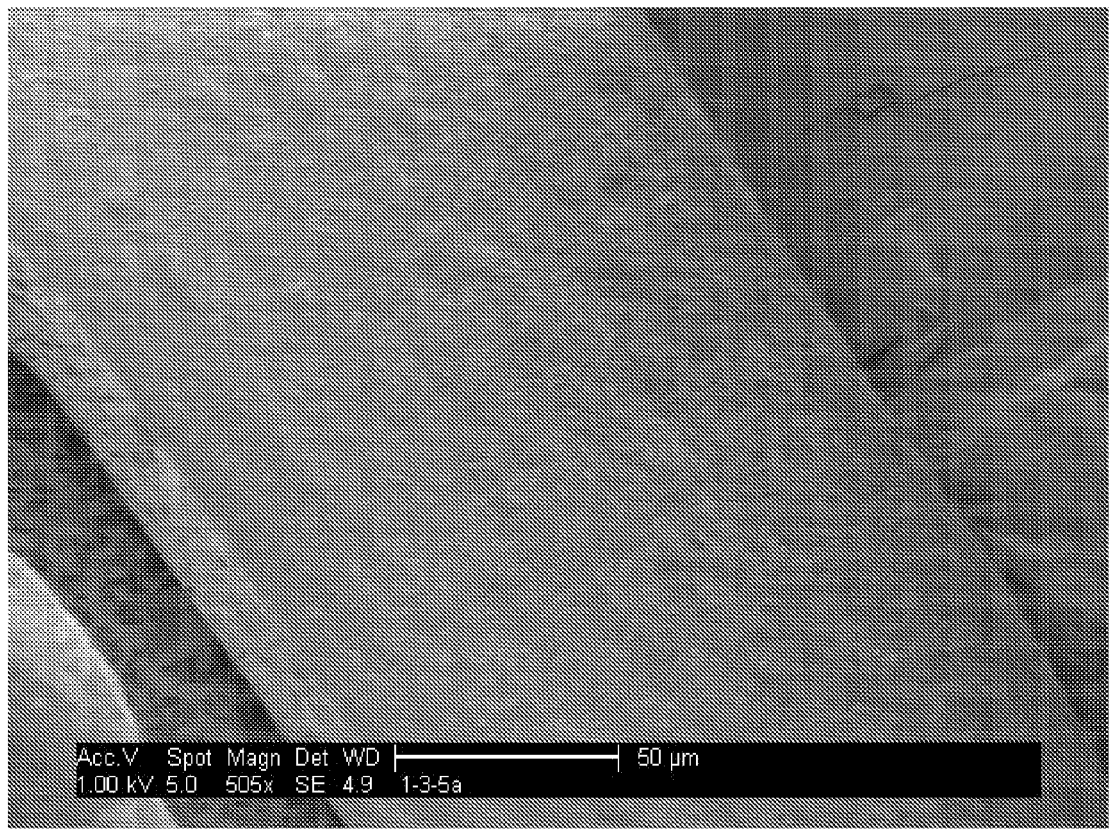
FIG. 10 is a Scanning Electron Micrograph at 500× magnification of ibuprofen/silicon-dioxide blend after 10 minutes in Example 1.
Figure 11:
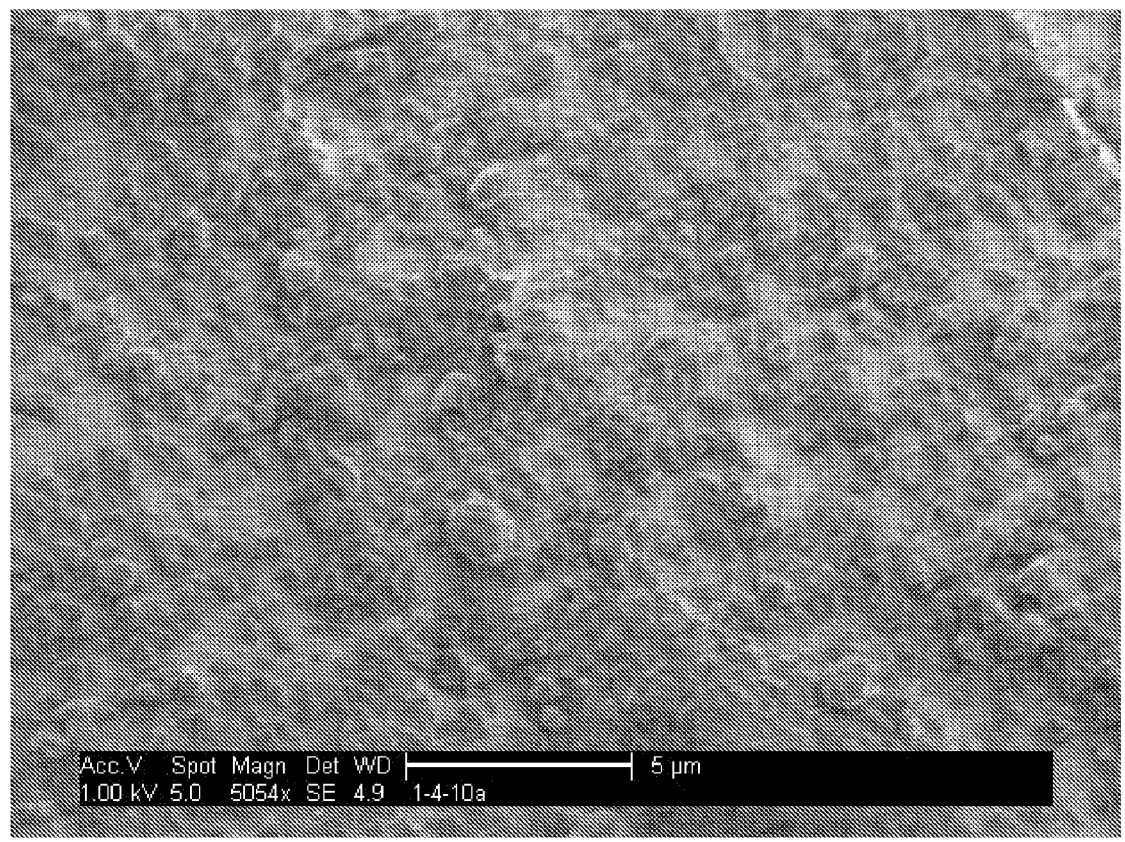
FIG. 11 is a Scanning Electron Micrograph at 5000× magnification of ibuprofen/silicon-dioxide blend after 10 minutes in Example 1.
Figure 12:
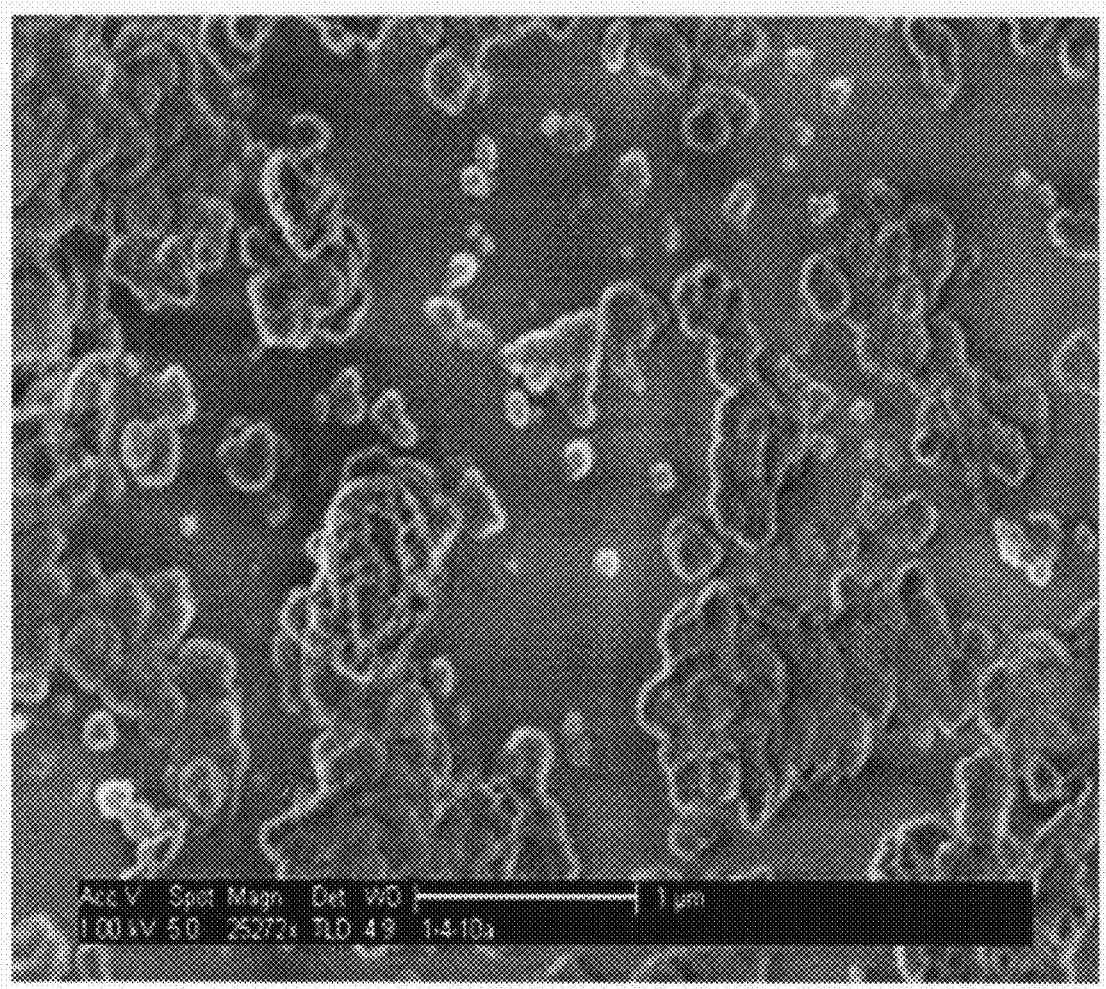
FIG. 12 is a Scanning Electron Micrograph at 25000× magnification of ibuprofen/silicon-dioxide blend after 10 minutes in Example 1.
Figure 13:
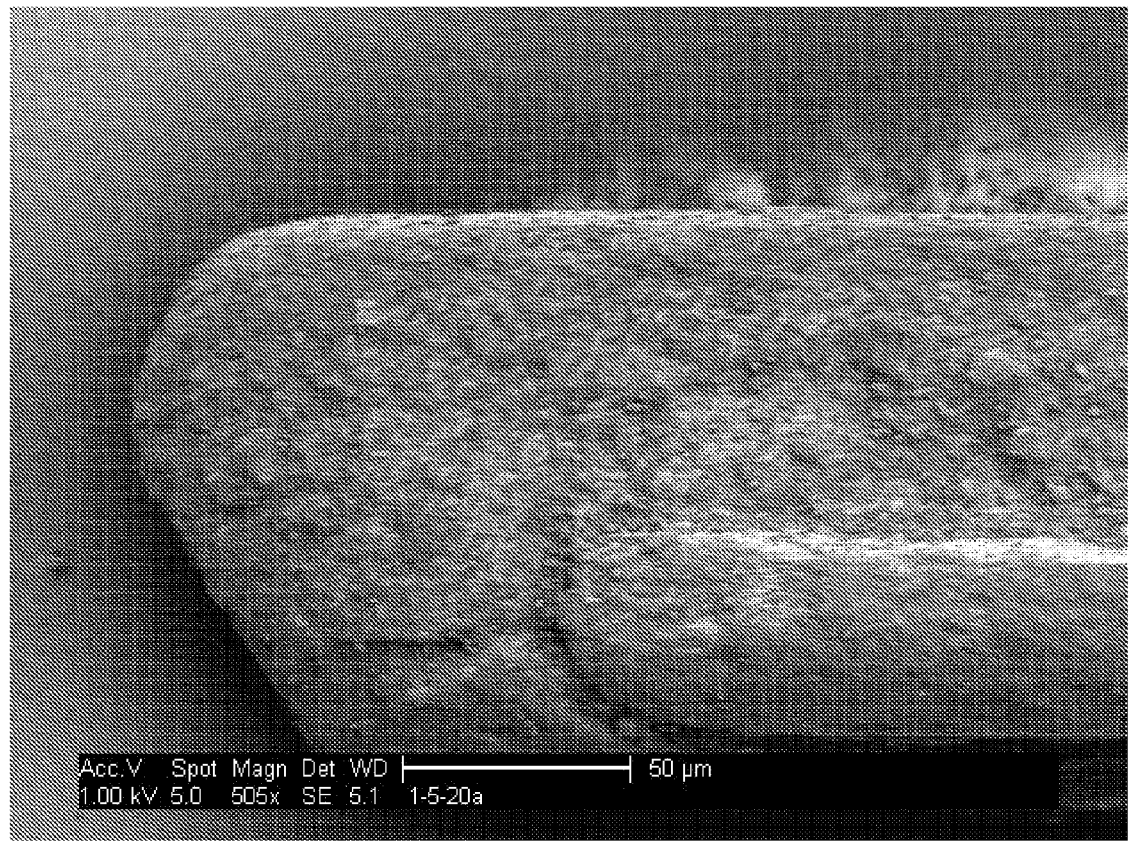
FIG. 13 is a Scanning Electron Micrograph at 500× magnification of ibuprofen/silicon-dioxide blend after 20 minutes in Example 1.
Figure 14:
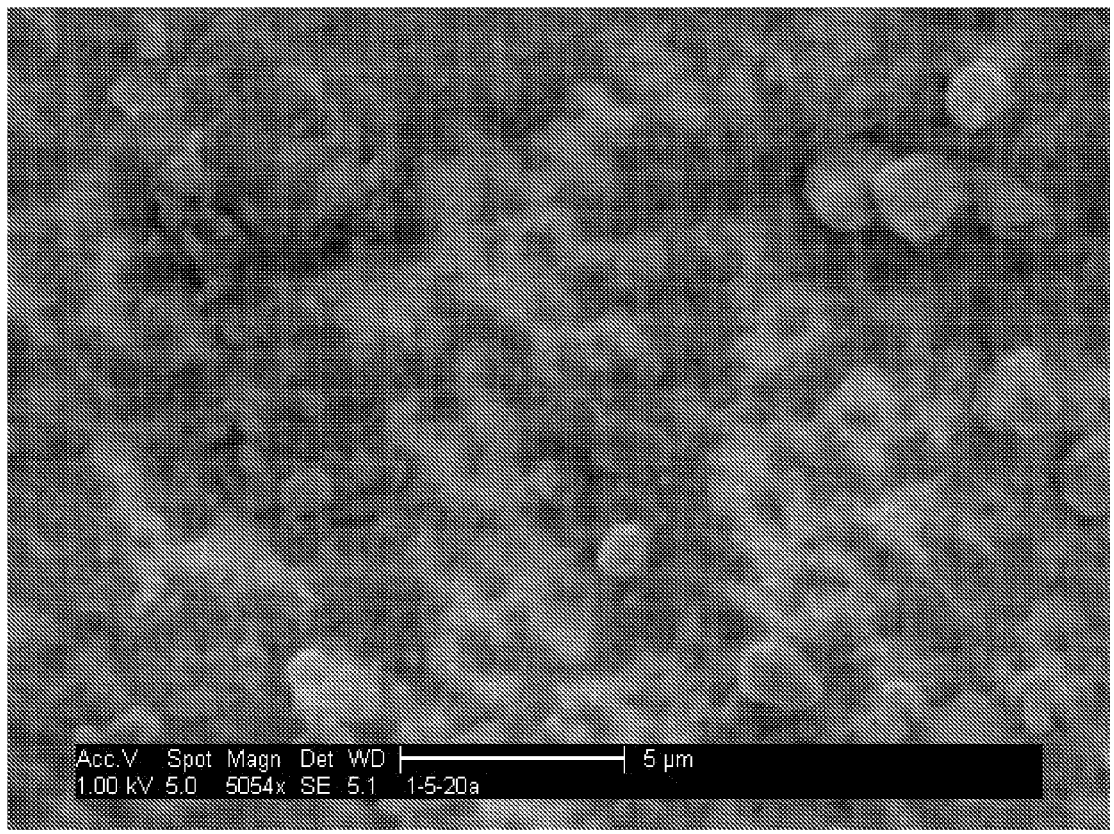
FIG. 14 is a Scanning Electron Micrograph at 5000× magnification of ibuprofen/silicon-dioxide blend after 20 minutes in Example 1.
Figure 15:
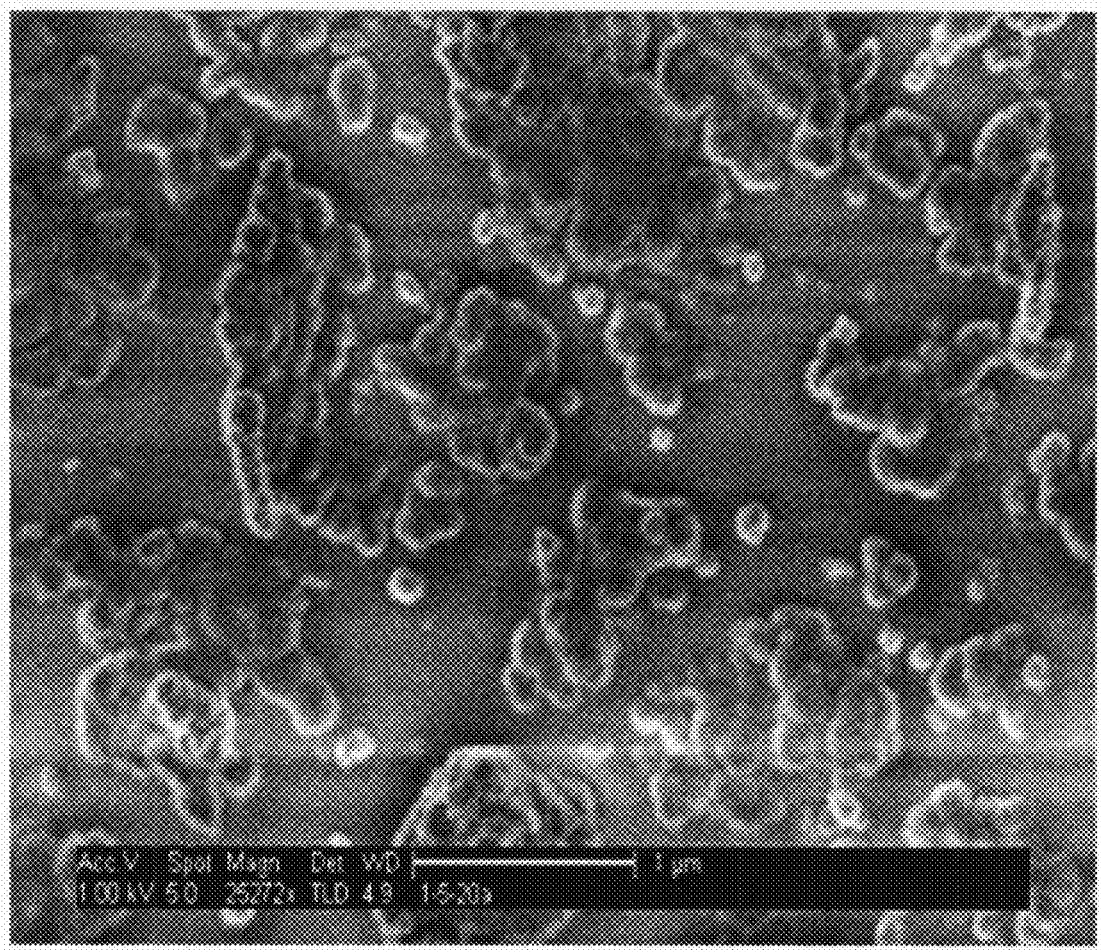
FIG. 15 is a Scanning Electron Micrograph at 25000× magnification of ibuprofen/silicon-dioxide blend after 20 minutes in Example 1.
Figure 16:
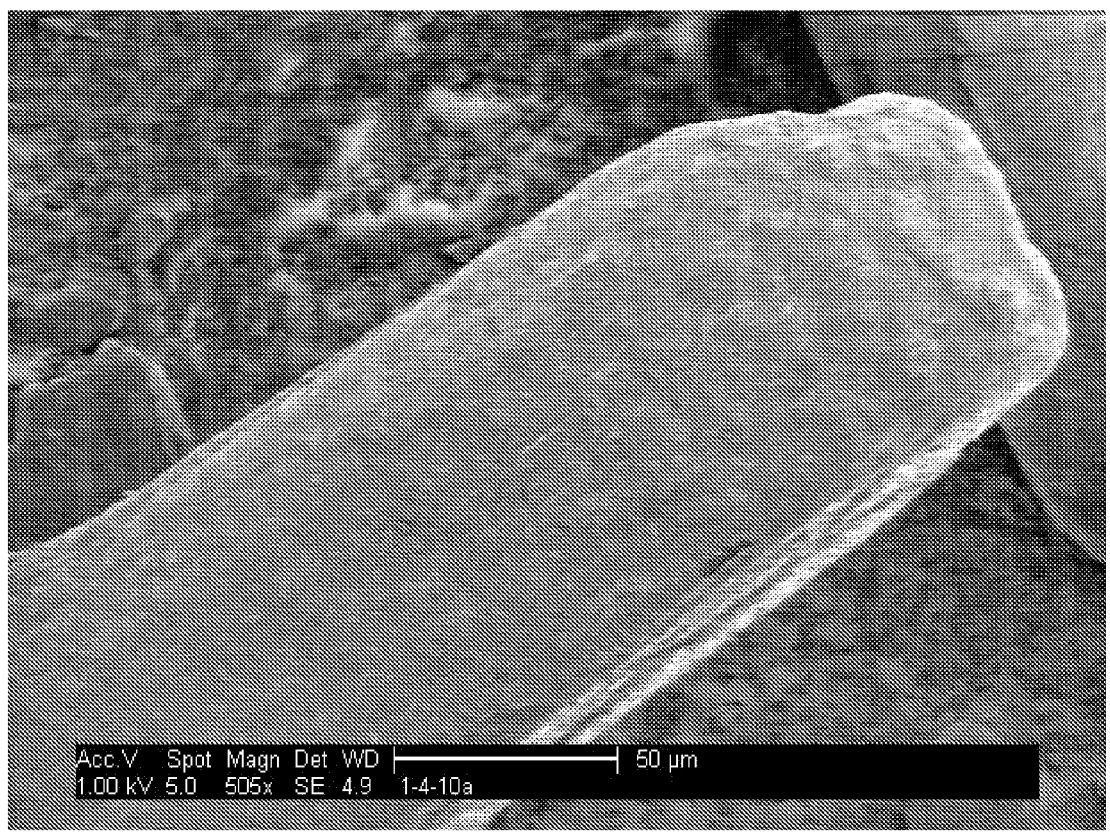
FIG. 16 is a Scanning Electron Micrograph at 500× magnification of ibuprofen/silicon-dioxide blend after 40 minutes in Example 1.
Figure 17:
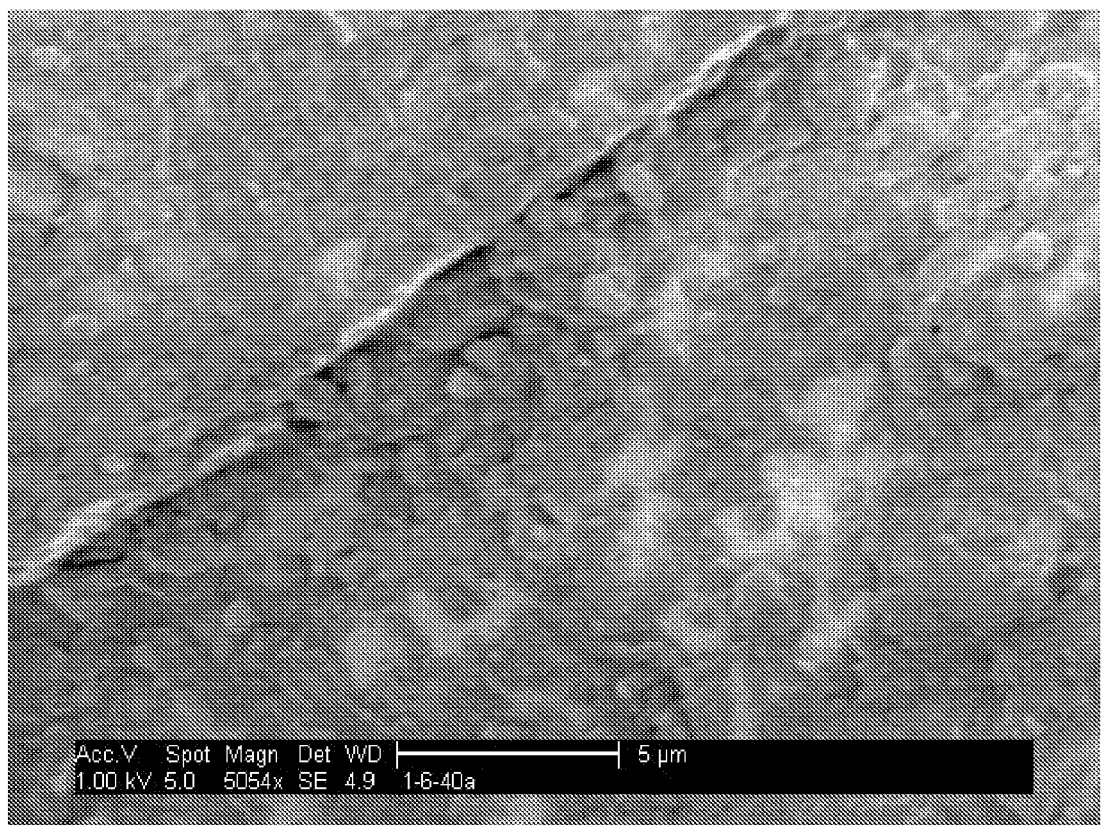
FIG. 17 is a Scanning Electron Micrograph at 5000× magnification of ibuprofen/silicon-dioxide blend after 40 minutes in Example 1.
Figure 18:
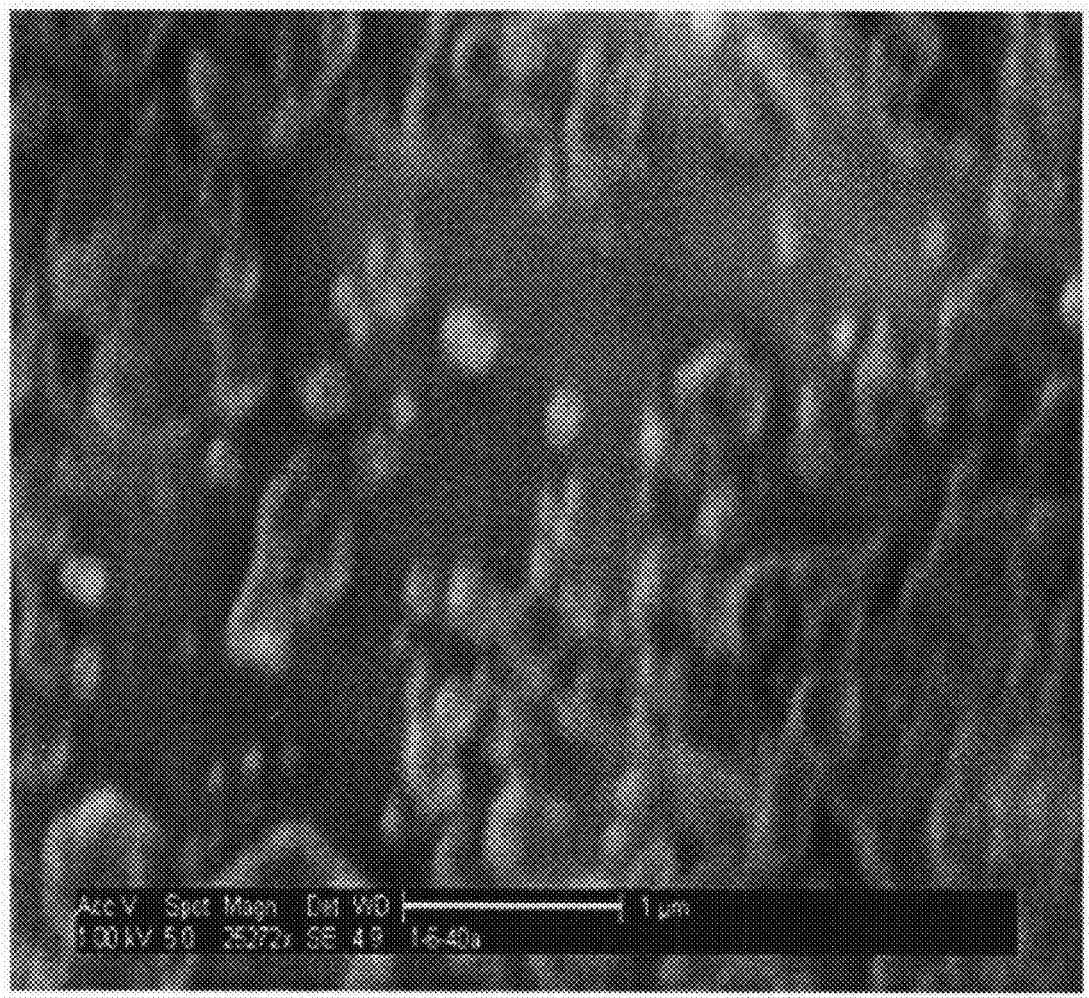
FIG. 18 is a Scanning Electron Micrograph at 25000× magnification of ibuprofen/silicon-dioxide blend after 40 minutes in Example 1.
Figure 19:
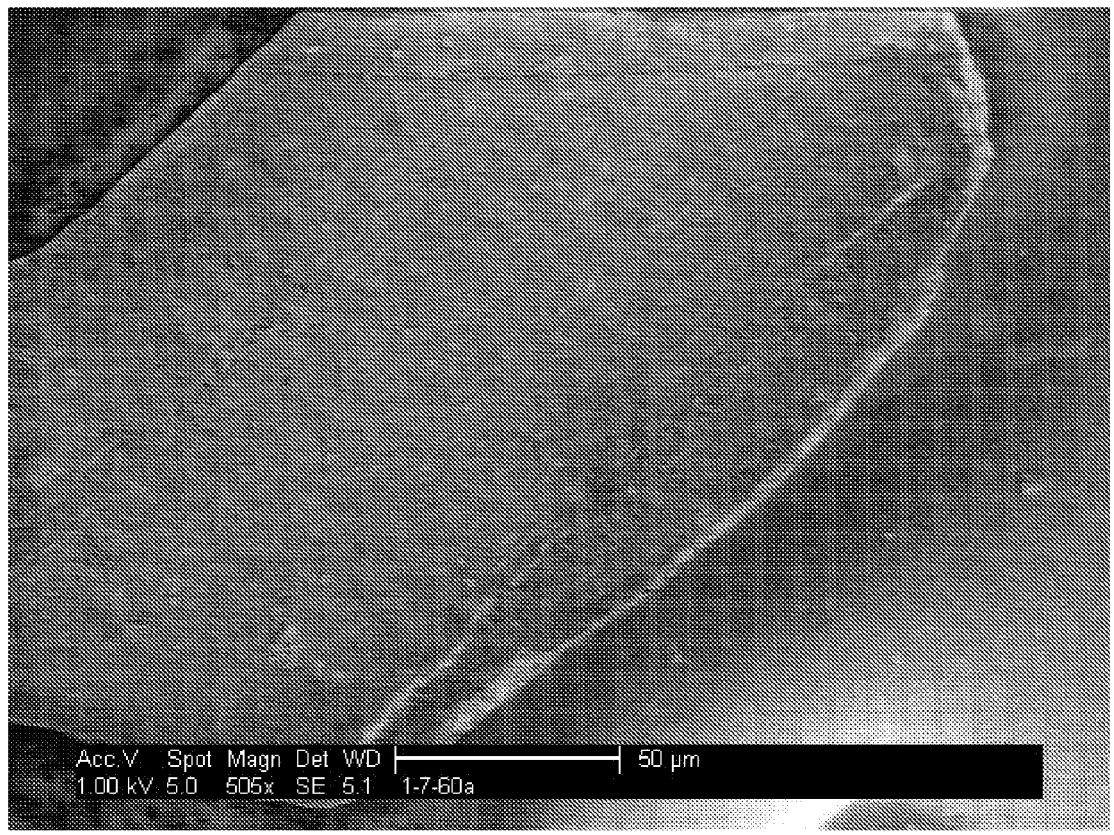
FIG. 19 is a Scanning Electron Micrograph at 500× magnification of ibuprofen/silicon-dioxide blend after 60 minutes in Example 1.
Figure 20:
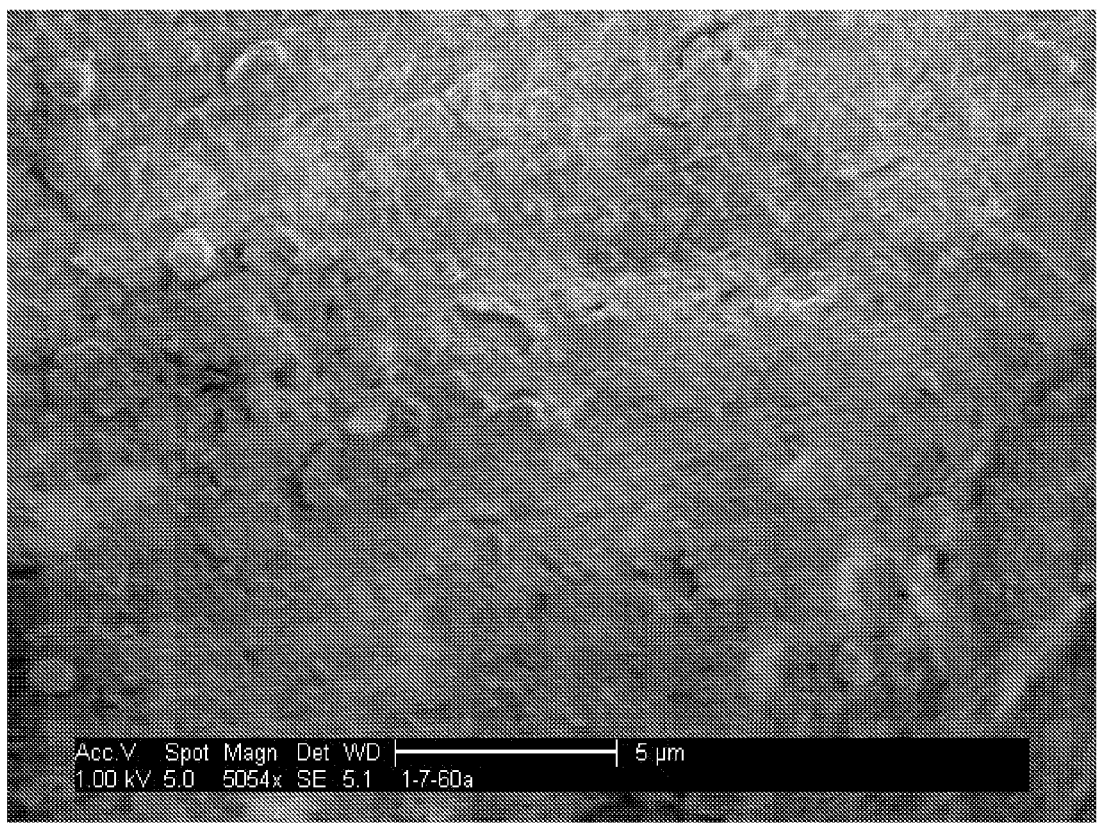
FIG. 20 is a Scanning Electron Micrograph at 5000× magnification of ibuprofen/silicon-dioxide blend after 60 minutes in Example 1.
Figure 21:
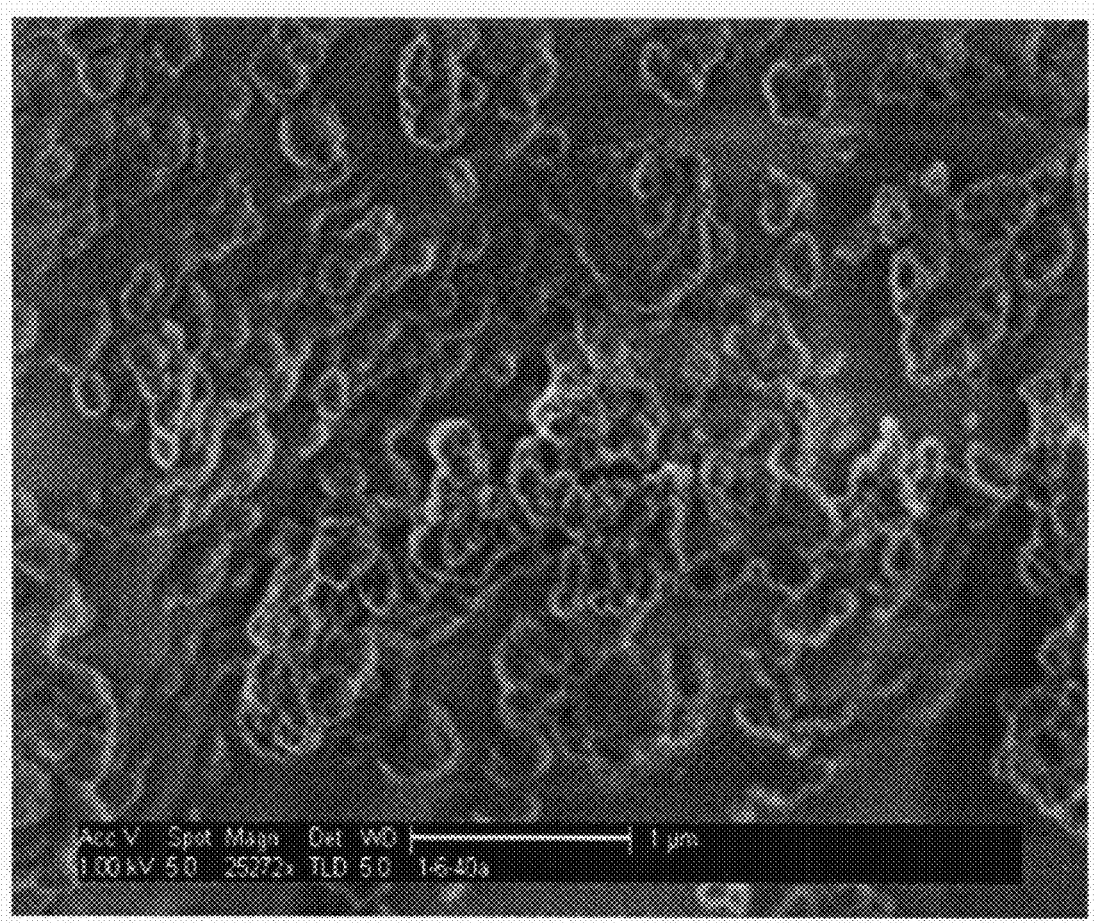
FIG. 21 is a Scanning Electron Micrograph at 25000× magnification of ibuprofen/silicon-dioxide blend after 60 minutes in Example 1.

SEM as a tool appears capable of discriminating between ibuprofen and silicon dioxide based on obvious morphological differences in the two components. For example, in FIGS. 1-3, ibuprofen crystals have a smooth flat appearance while in FIGS. 4-6 silicon dioxide appears as ball-like shapes. The added feature of elemental analysis on the same instrument and at high resolution confirms the morphological differences. There is a progressive change in the appearance of the ibuprofen/silicon dioxide agglomerates with the increase of mixing time. The coverage appears to increase markedly in both low resolution and high resolution images taken from similar aspects on similar crystals of ibuprofen. On high resolution images coverage also changes in qualitative aspects, with the silicon dioxide being altered in appearance from primarily colloidal ball like structures. As shown in FIGS. 7-9 the silicon dioxide at the later blend times seems to adopt plate-like or sheet-like structures that comprehensively cover the ibuprofen crystals as shown in FIGS. 19-21.

Example 2

An embodiment was utilized in a tablet manufacturing process comprising a pre-blending step, two blending steps and tablet compression. In this embodiment, only ibuprofen and silicon dioxide were used in the pre-blending step, as shown in Blend Step 1.

The tablet formulation additionally comprised Hypermellose (Hydroxypropyl Methylcellulose) K4M and K100LV, Microcrystalline Cellulose, (Prosolv) SMCC50 and SMCC 90, Croscarmellose Sodium (AcDiSol), Glycine, stearic acid and additional silicon dioxide.

| Tablet Formulation | | |
|---|---|---|
| Ingredient | Function | Amount (mg) |
| Ibuprofen | Active Pharmaceutical | 600 |
| Silicon Dioxide | Blend Additive | 6 |
| Hypermellose (Hydroxypropyl Methylcellulose) K4M | Hydrophilic Polymer | 125 |
| Hypermellose (Hydroxypropyl Methylcellulose) K100LV | Hydrophilic Polymer | 65 |
| Microcrystalline Cellulose, (Prosolv) SMCC50 | Formulation Additive | 200 |
| Microcrystalline Cellulose, (Prosolv) SMCC90 | Formulation Additive | 100 |
| Croscarmellose Sodium (AcDiSol) | Dissolution Additive | 35 |
| Glycine | Dissolution Additive | 50 |
| Stearic Acid | Lubricant | 12 |
| Silicon Dioxide | Flow Agent | 6 |
| Total Tablet Weight | | 1199 |

| Pre-Blend Step 1 | | |
|---|---|---|
| Ingredient | Function | Amount (mg) |
| Ibuprofen | Active Pharmaceutical | 600 |
| Silicon Dioxide | Blend Additive | 6 |

These components were passed through a 30-mesh screen. The screened components were then blended in a V-blender for 60 minutes.

| Blend Step 1 | | |
|---|---|---|
| Ingredient | Function | Amount (mg) |
| Ibuprofen and Silica Blend | Pre-Blend 1 | 606 |
| Hypermellose (Hydroxypropyl Methylcellulose) K4M | Hydrophilic Polymer | 125 |
| Hypermellose (Hydroxypropyl Methylcellulose) K100LV | Hydrophilic Polymer | 65 |
| Microcrystalline Cellulose, (Prosolv) SMCC50 | Formulation Additive | 200 |
| Microcrystalline Cellulose, (Prosolv) SMCC90 | Formulation Additive | 100 |
| Croscarmellose Sodium (AcDiSol) | Dissolution Additive | 35 |
| Glycine | Dissolution Additive | 50 |

The components not contained within pre-blend step 1 were passed through a 30-mesh screen. All components were then blended in a V-blender until content uniformity was achieved.

| Blend Step 2 | | |
|---|---|---|
| Ingredient | Function | Amount (mg) |
| Ibuprofen, Silica, HPMC, MCC, Croscarmellose Sodium, Glycine | Blend 1 | 1181 |
| Stearic Acid | Lubricant | 12 |
| Silicon Dioxide | Flow Agent | 6 |
| Total Uncompressed Tablet Formulation | | 1199 |

The components not contained within the Pre-Blending step were passed through a 30-mesh screen. All components were then blended in a V-blender for 5 minutes. In this embodiment, the silica contained in Blend Step 2 was employed as a glidant rather than as a blend additive.

Tablet Compression

The uncompressed tablet formulation resulting from Blend Step 3 was then loaded into a rotary tablet pressed and compressed without requiring any additional processing steps.

Example 3

In another embodiment, the formulation comprised ibuprofen, hydroxypropyl methylcellulose (HPMC K4M), sodium carbonate, arginine, flow agents and tableting aids, in which HPMC K4M was present at a concentration of 32% by weight of ibuprofen, sodium carbonate was present at concentration of 17% by weight of the ibuprofen, and arginine was present at a concentration of 17% by weight of ibuprofen within a compressed monolithic tablet.

| Ex. 3 | mg |
|---|---|
| Ibuprofen 90 grade | 600 |
| Silica | 5.5 |
| MCC PH 105 | 210 |
| HPMC K4M Prem | 190 |
| $Na_2CO_3$ anhydrous | 100 |
| MCC PH 200 | 100 |
| Arginine | 100 |
| Silica | 5.5 |
| Stearic Acid | 12 |
| Total: | 1323 |

The microcrystalline cellulose PH 105 and 5.5 mg of silica were pre-blended n a V-blender with ibuprofen to form a pre-blended powder. The remaining excipients were blended with the resulting pre-blended powder. The resulting tableting formulation was compressed into tablets using conventional technologies.

Figure 23:
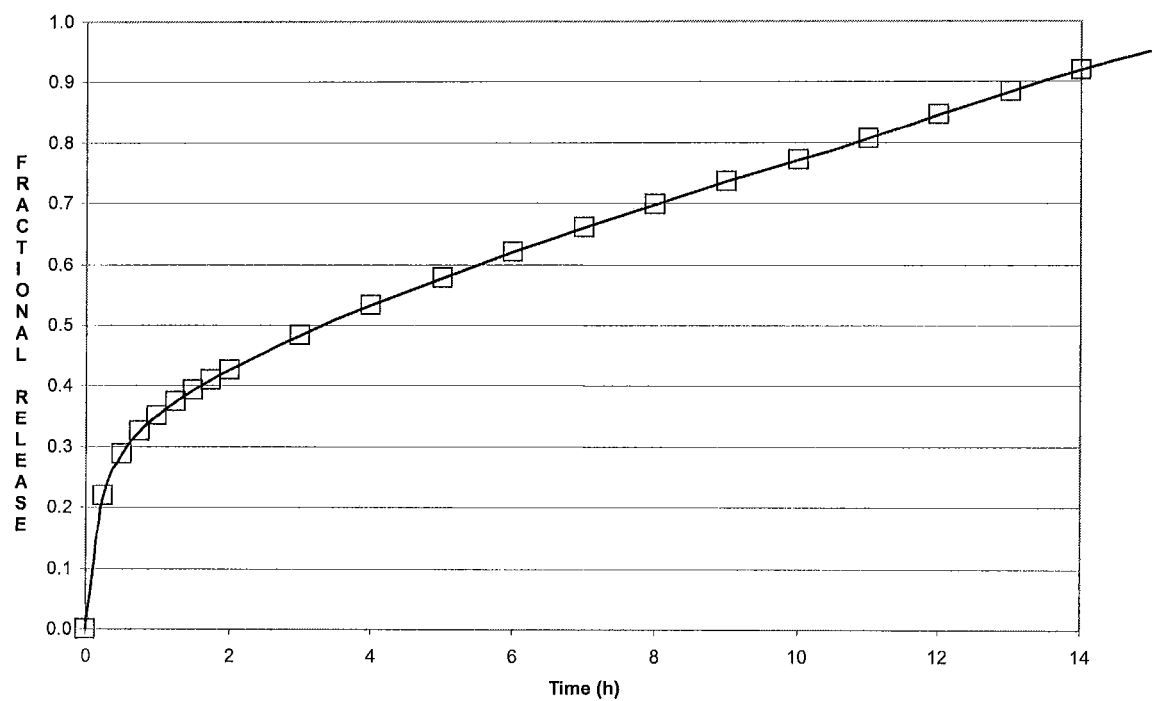
FIG. 23 is a graph illustrating the in vitro release profile from Example 3.

As shown in FIG. 23, the results of this Example demonstrate the in vitro release profile comprising a burst effect, followed by the sustained release of the remaining material. The initial release is greater than 20% of ibuprofen in less than two hours, and approximately 90% release over a period of 14 hours.

Example 4

In another embodiment, the formulation comprised two viscosities of HPMC, two particle sizes of silicified MCC, in combination with croscarmellose and glycine, and a stearic acid lubricant, in which the combined HPMC was present at about 32% based on the ibuprofen present in the formulation in HPMC K100LV and HPMC K4M were present in a weight ratio of about 2:1 respectively, and silicified MCC was present as Prosolv50 and Prosolv90 in a weight ratio of about 2:1 at a combined concentration of about 50% based on the ibuprofen present in the formulation within a monolithic tablet.

| Ex. 4 | mg/tablet |
|---|---|
| HPMC K4M | 125 |
| HPMV K100LV | 65 |
| MCC (Prosolv SMCC 50, approx 60 um) | 200 |
| MCC (Prosolv SMCC 90, approx 110 um) | 100 |
| Croscarmellose Sodium (AcDiSol) | 35 |
| Glycine | 50 |
| Ibuprofen, (90 grade) | 600 |
| Silicon Dioxide | 12 |
| Stearic Acid | 12 |
| Total | 1199 |

Figure 24:
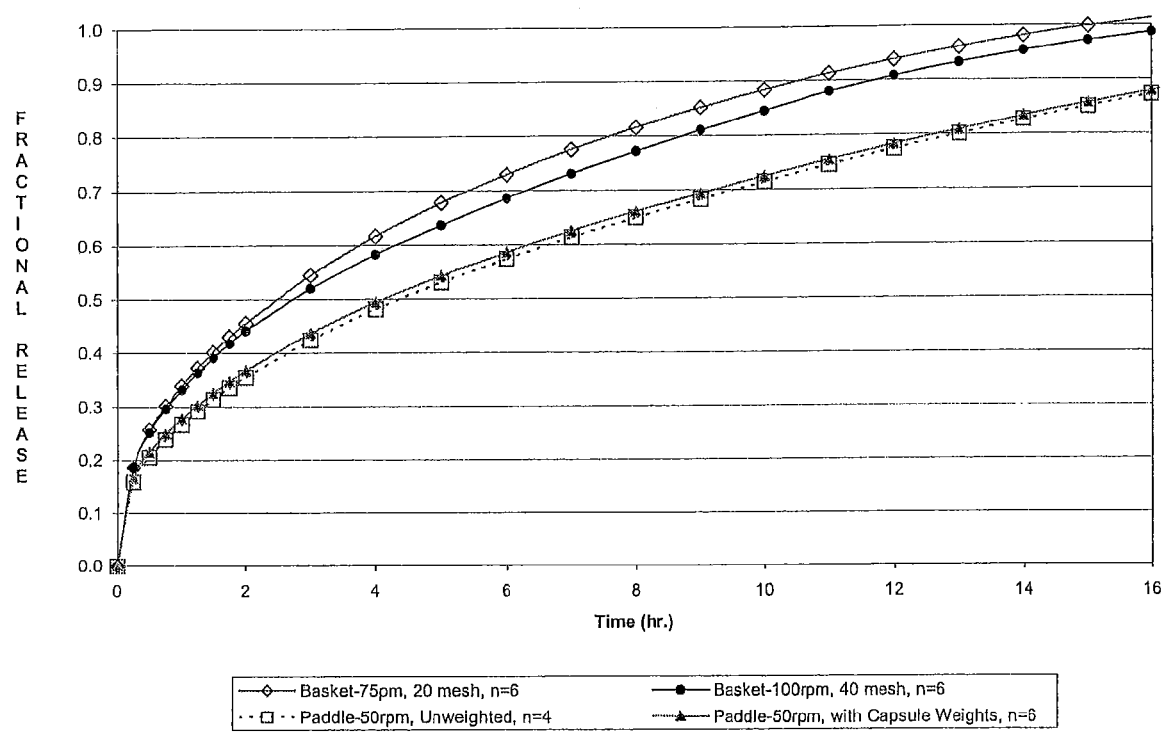
FIG. 24 is a graph illustrating the in vitro release profile from Example 4.

All ingredients were passed through a 30-mesh screen. The ibuprofen was pre-blended with the 6 mg silica at about a 1:100 ratio in a V-blender. The resulting pre-blended ibuprofen powder was blended with the remaining excipients. The resulting powder was compressed into tablets using conventional technologies. The results of this Example, shown in FIG. 24, demonstrate the invention is capable of an in vitro release profile comprising a burst effect, followed by the sustained release of the remaining material over a period of 16 hours, with greater than 30% release occurring within 2.0 hours.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

We claim:

1. A method of forming a tablet comprising the steps of pre-blending for a time between 15 minutes and 90 minutes an active pharmaceutical ingredient susceptible to tackiness and a blending additive consisting of silicon dioxide, silicified microcrystalline cellulose or a combination thereof with a first mixing effort to form a pre-blend mixture, mixing at least one excipient and said pre-blend mixture with a second mixing effort to form a blend suitable for direct compression and compressing said blend to form said tablet.

2. The method of claim 1, wherein said active pharmaceutical ingredient comprises ibuprofen.

3. The method of claim 2, wherein the pre-blending step comprises pre-blending for a time between 20 minutes and 90 minutes.

4. The method of claim 2, wherein the pre-blending step comprises pre-blending for a time between 40 minutes and 60 minutes.

5. The method of claim 1, wherein said blending additive is present at a concentration in the range of 0.1% to 10% by weight of said active pharmaceutical ingredient.

6. The method of claim 2, wherein said blending additive is present at a concentration in the range of 0.5% to 1.5% by weight of said active pharmaceutical ingredient.

7. A method of forming a tablet comprising the steps of:
   a. pre-blending for a time between 15 minutes and 90 minutes an active pharmaceutical ingredient susceptible to tackiness and a first blending additive consisting of silicon dioxide, silicified microcrystalline cellulose or a combination thereof with a first mixing effort to form a pre-blend mixture;
   b. blending said pre-blend mixture with at least one excipient with a second mixing effort to form a first blend;
   c. blending said blend from step b with a second blending additive with a third mixing effort, wherein said first mixing effort, said second mixing effort and said third mixing effort form a second blend suitable for direction compression; and
   d. compressing said second blend from step c to form said tablet.

8. The method of claim 7, wherein said active pharmaceutical ingredient comprises ibuprofen.

9. The method of claim 8, wherein the pre-blending step comprises pre-blending for a time between 20 minutes and 90 minutes.

10. The method of claim 8, wherein the pre-blending step comprises pre-blending for a time between 40 minutes and 60 minutes.

11. The method of claim 8, wherein said first blending additive is present at a concentration in the range of 0.1% to 10% by weight of said active pharmaceutical ingredient.

12. The method of claim 8, wherein said first blending additive is present at a concentration in the range of 0.5% to 1.5% by weight of said active pharmaceutical ingredient.

13. A method of forming a tablet comprising the steps of pre-blending for a time between 15 minutes and 90 minutes only ibuprofen and silicon dioxide with a first mixing effort to form a pre-blend mixture, mixing at least one excipient with said pre-blend mixture with a second mixing effort to form a blend suitable for direct compression, and compressing said blend to form said tablet.

14. The method of claim 13, wherein the pre-blending step comprises pre-blending for a time between 40 minutes and 60 minutes.

15. The method of claim 13, wherein said silicon dioxide is present at a concentration in the range of 0.5% to 1.5% by weight of said ibuprofen.

16. A method of forming a tablet consisting essentially of the steps of:
   a. pre-blending only ibuprofen and silicon dioxide with a first mixing effort to form a pre-blend mixture;
   b. blending said resulting pre-blend mixture with at least one excipient with a second mixing effort to form a first blend;
   c. blending said first blend from step b with at least one blending additive with a third mixing effort, wherein said first mixing effort, said second mixing effort and said third mixing effort form a second blend suitable for direction compression; and
   d. compressing said second blend from step c to form said tablet.

17. A method of forming a tablet consisting essentially of the steps of:
   a. pre-blending only ibuprofen and a blending additive consisting of silicon dioxide, silicified microcrystalline cellulose or a combination thereof with a first mixing effort to form a pre-blend mixture;
   b. blending said resulting pre-blend mixture with at least one excipient with a second mixing effort to form a first blend suitable for compression; and
   c. compressing said first blend from step b to form said tablet.

18. A method of claim 17, wherein said blending additive consists of silicon dioxide.

19. A method of claim 18, wherein said silicon dioxide is present in the amount of 0.01% by weight of said ibuprofen.

20. A method of claim 17, wherein the pre-blending step comprises pre-blending for a time between 15 minutes and 60 minutes.

* * * * *